US011717611B2

(12) United States Patent
Cowe et al.

(10) Patent No.: US 11,717,611 B2
(45) Date of Patent: Aug. 8, 2023

(54) MEDICAMENT DELIVERY DEVICES

(71) Applicant: Owen Mumford Limited, Oxford (GB)

(72) Inventors: Toby Cowe, Oxfordshire (GB); Colin Webb, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 991 days.

(21) Appl. No.: 16/462,139

(22) PCT Filed: Nov. 17, 2017

(86) PCT No.: PCT/GB2017/053470
§ 371 (c)(1),
(2) Date: May 17, 2019

(87) PCT Pub. No.: WO2018/091917
PCT Pub. Date: May 24, 2018

(65) Prior Publication Data
US 2019/0328973 A1  Oct. 31, 2019

(30) Foreign Application Priority Data

Nov. 18, 2016  (GB) ..................... 1619562

(51) Int. Cl.
*A61M 5/20* (2006.01)
*A61M 5/24* (2006.01)
(Continued)

(52) U.S. Cl.
CPC ........ *A61M 5/2066* (2013.01); *A61M 5/2033* (2013.01); *A61M 5/2429* (2013.01);
(Continued)

(58) Field of Classification Search
CPC .... A61M 5/19; A61M 5/2033; A61M 5/2429; A61M 5/2448; A61M 5/284;
(Continued)

(56) References Cited

U.S. PATENT DOCUMENTS 10,300,213 B2   5/2019  Bengtsson et al.
10,478,552 B2  11/2019  Cronenberg et al.
(Continued)

FOREIGN PATENT DOCUMENTS

CN    105939742 A    9/2016
EP    2 944 340 A1  11/2015
(Continued)

OTHER PUBLICATIONS

First Office Action from corresponding Chinese Patent Application No. 201780083597.2, dated Apr. 6, 2021 (29 pages) (English translation included).
(Continued)

*Primary Examiner* — Tiffany Legette
(74) *Attorney, Agent, or Firm* — Quarles & Brady LLP

(57) ABSTRACT

A medicament delivery device (100) for delivery of medicament from a cartridge (10) into an injection site, through a cannula (134). The cartridge has a medicament chamber (14) with an outlet (15), and a sealing element (16) for closing the outlet (15). The device has a housing (102) for receiving the cartridge (10), and a drive mechanism (200) to expel the medicament from the device upon activation of the drive mechanism (200). The device has a connection arrangement (199) comprising a hub (166) and spring means (184) for driving relative movement between the hub (166) and the cartridge (10) upon operation of an operating member (190). The operating member switches the connection arrangement (199) from an unconnected configuration to a connected configuration, in which the hub (166) cooperates with the cartridge (10) to open the outlet (15). When connected, fluid may flow between the chamber (14) and the cannula (134).

77 Claims, 29 Drawing Sheets

(51) Int. Cl.
    *A61M 5/315* (2006.01)
    *A61M 5/31* (2006.01)
(52) U.S. Cl.
    CPC ...... *A61M 5/3158* (2013.01); *A61M 5/31596* (2013.01); *A61M 2005/206* (2013.01); *A61M 2005/2073* (2013.01); *A61M 2005/3128* (2013.01); *A61M 2005/31518* (2013.01)
(58) Field of Classification Search
    CPC .... A61M 5/285; A61M 5/31596; A61M 5/20; A61M 5/2066; A61M 2005/2073
    See application file for complete search history.

(56) References Cited

U.S. PATENT DOCUMENTS

| | | |
|---|---|---|
| 2005/0203461 A1 | 9/2005 | Flaherty et al. |
| 2013/0006213 A1 | 1/2013 | Arnitz et al. |
| 2014/0025014 A1 | 1/2014 | Radmer et al. |
| 2016/0082241 A1 | 3/2016 | Burton et al. |
| 2017/0007775 A1* | 1/2017 | Bengtsson .......... A61M 5/3202 |
| 2017/0143902 A1* | 5/2017 | Hansen ............... A61M 5/3245 |

FOREIGN PATENT DOCUMENTS

| | | |
|---|---|---|
| WO | 2011146166 A1 | 11/2011 |
| WO | WO 2015/081337 A2 | 6/2015 |
| WO | WO 2015/197866 A1 | 12/2015 |

OTHER PUBLICATIONS

First Office Action from corresponding Japanese Patent Application No. 2019-526580 dated Jul. 26, 2021 (10 pages) English translation included.

May 9, 2018 Transmittal of ISR and Written Opinion of Int'l Searching Authority for PCT/GB2017/053470.

* cited by examiner

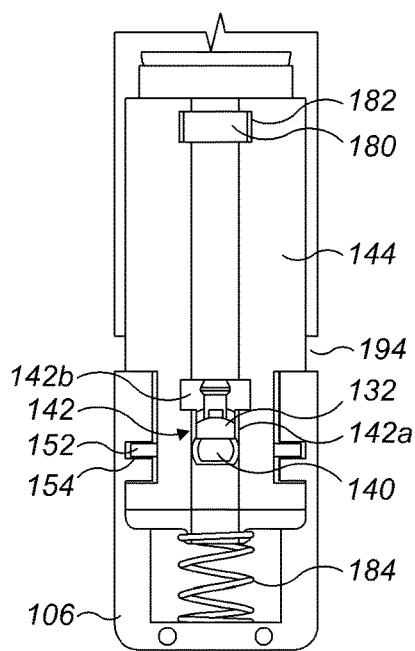 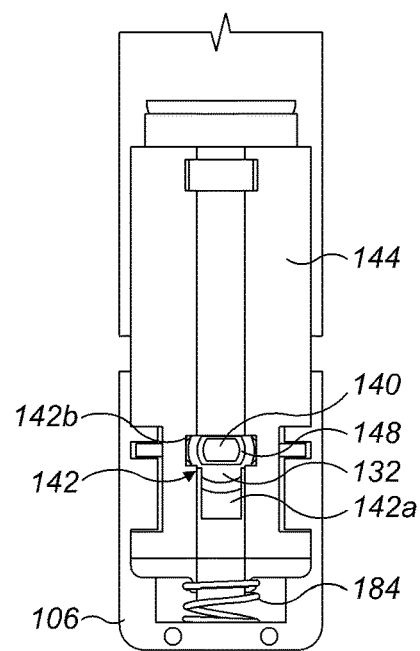
FIG. 14(a)  FIG. 14(b)
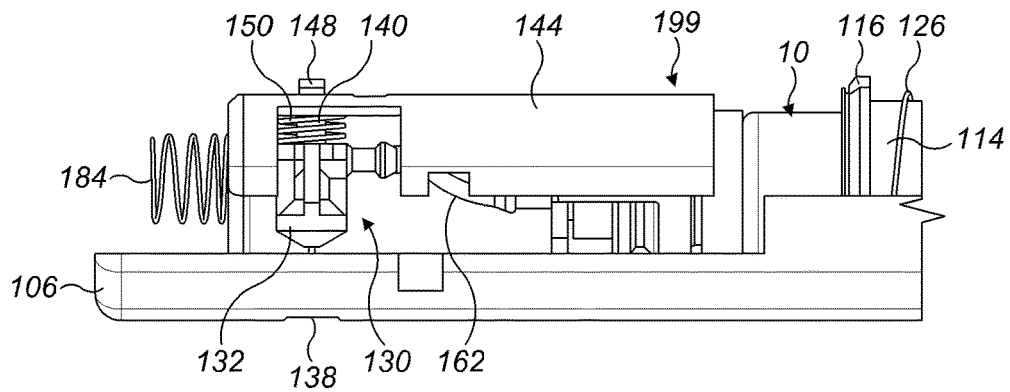
FIG. 15(a)
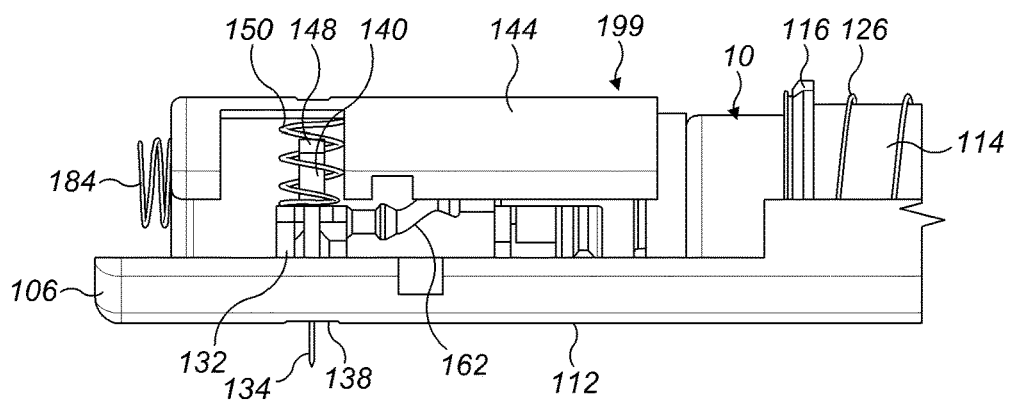
FIG. 15(b)

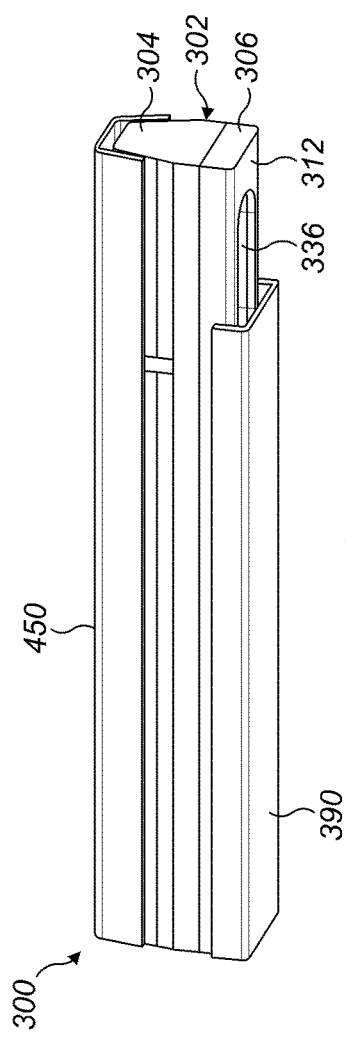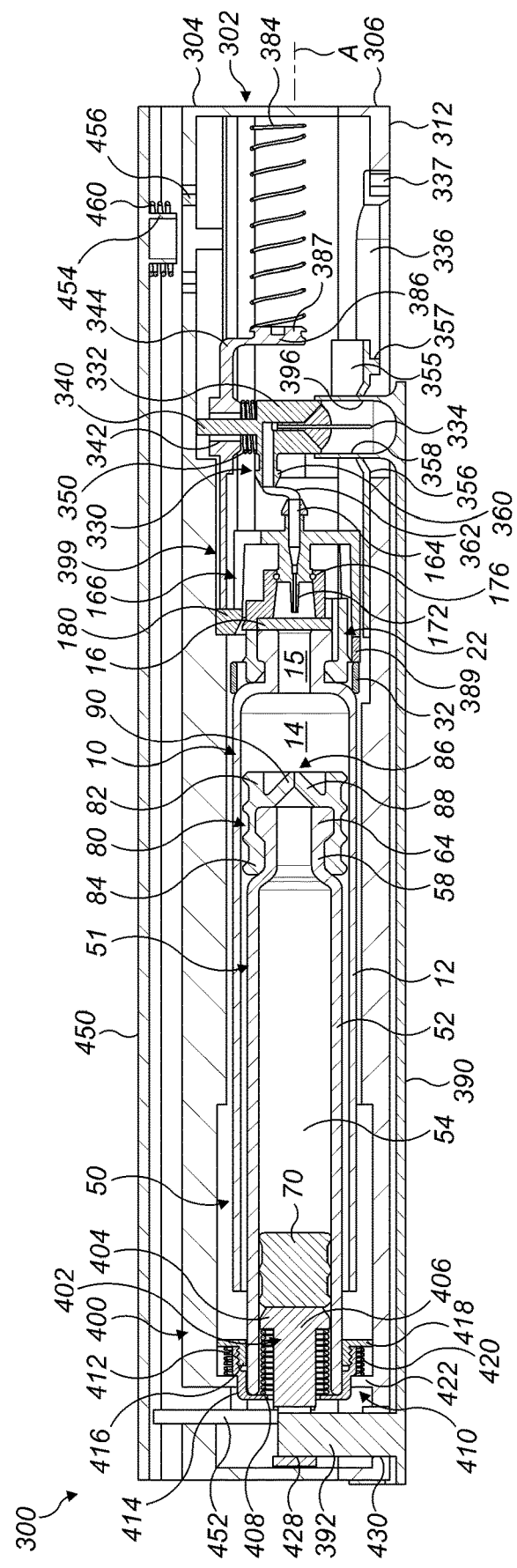

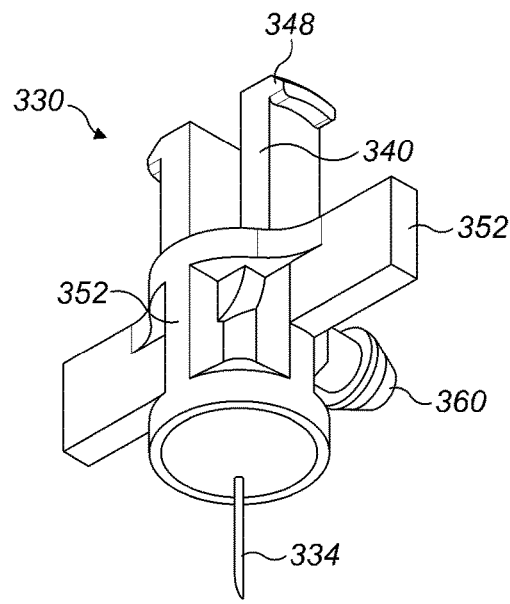
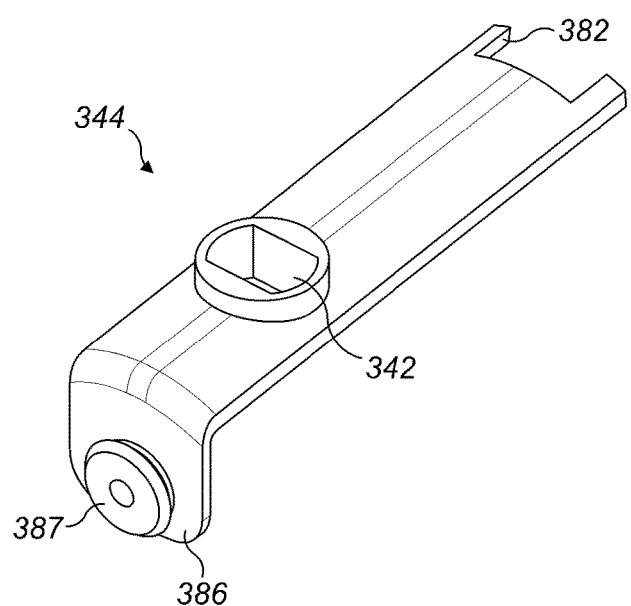
FIG. 21
FIG. 22
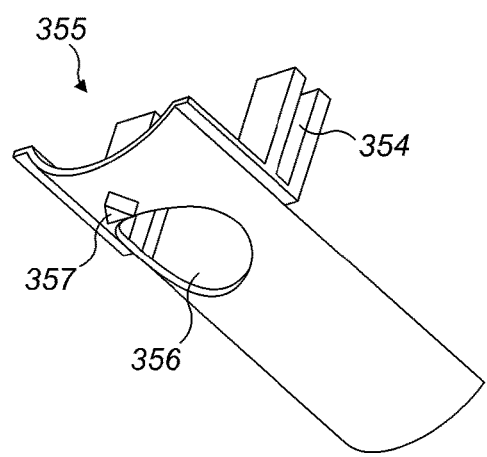
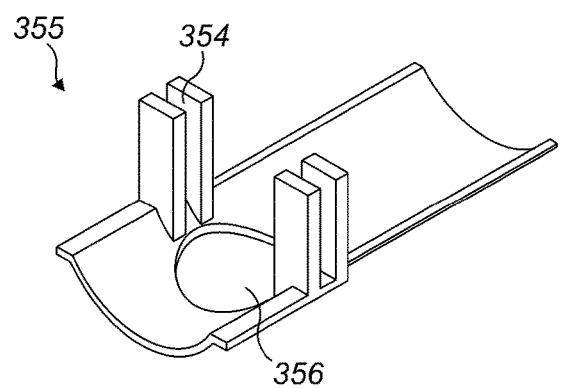
FIG. 23(a)
FIG. 23(b)

MEDICAMENT DELIVERY DEVICES

The present application is a § 371 submission of international application no. PCT/GB2017/053470, filed 17 Nov. 2017 and titled Medicament Delivery Devicea, which was published in the English language on 24 May 2018 with publication no. WO 2018/091917 A1, and which claims the benefit of the filing date of GB 16 19562.0 filed 18 Nov. 2016, the contents of which are incorporated herein by reference.

This invention relates to devices suitable for delivering medicament substances to a patient. In particular, but not exclusively, the invention relates to wearable medicament delivery devices for the delivery of liquid or reconstitutable medicaments. This invention further relates to medicaments, including pharmaceutical compositions, for subcutaneous injection or infusion disposed within the delivery devices and methods of treating patients with conditions susceptible to treatment by delivering the medicament using the delivery devices described herein.

Medicaments for subcutaneous injection or infusion are used in therapy in various different clinical situations. Administration of medicaments by a patient themselves (self-administration) or by a carer who is not medically trained is becoming increasingly important for reducing care costs and reducing patient dependency on clinical staff and facilities.

To this end, a variety of devices have been developed that are suitable for delivery of injectable medicaments in a non-clinical environment by a patient or carer. Typically, in such devices, at least part of the operational sequence of the device is automated.

For example, injection devices designed for automatic needle insertion and injection of a single pre-determined dose of a medicament are known in the art as auto-injectors. Such devices typically include a housing that allows the user to grip the device, a pre-filled syringe containing the medicament, and a drive mechanism. The pre-filled syringe includes a tubular glass barrel with a staked hypodermic needle at its distal end, a needle shield to protect and seal the needle, and a stopper slidably received in the barrel. One example of a pre-filled syringe of this type is available under the registered trade mark Hypak (Becton Dickinson, New Jersey, USA).

The syringe is axially movable within the housing between an initial, retracted position in which the needle is retracted in the housing, and a deployed position in which the needle projects from the end of the housing. With the syringe in the retracted position, the distal end of the housing is closed by a cap. To prepare the device for use, the cap is removed. The cap is arranged to grip the rigid needle shield, so that removal of the cap pulls the rigid needle shield off the needle. The distal end of the housing is then placed against the skin, and the user operates a trigger of the device, such as a button, to activate the drive mechanism. The drive mechanism typically comprises a plunger that is biased in the distal direction by a compression spring. The plunger is initially held in an initial, latched position by a latch arrangement. Upon activation of the drive mechanism, the plunger is released from the latched position and can move distally under the force of the compression spring.

Initially, release of the plunger causes the syringe to move from the retracted position into the deployed position, so that the needle pierces the skin. Subsequently, the plunger forces the stopper in the distal direction to inject the medicament.

Auto-injectors of these types can be convenient for self-administration by a patient of a measured dose of a medicament, although they may also be used by trained medical personnel. In both cases, auto-injectors typically offer increased user safety compared with traditional syringes, for example by ensuring that the needle used to deliver the medicament is shrouded before and/or after delivery of the medicament, and by the inclusion of interlock means or other safety devices to prevent accidental operation of the device.

Existing auto-injector devices can however have several drawbacks. For example, one consequence of the linear arrangement of the device components is that the distal end of the device must be held firmly in contact with the injection site whilst the trigger is manipulated to activate the device and during subsequent delivery of the medicament. To ensure optimum needle penetration and to minimise discomfort, the body of the device should be held perpendicular to the injection site and with as little movement as possible. This may be relatively difficult for some users, such as individuals with reduced manual dexterity, impaired vision, and so on, and can be particularly problematic when injection takes place over a relatively long time period, such as when a high volume of medicament is to be delivered or when a high viscosity medicament is used.

A more suitable arrangement may be to provide a low-profile, wearable device having a relatively large contact face for placement against the injection site, with a needle that extends perpendicularly with respect to the contact face and in which a container for the medicament is arranged with an elongate axis of the container parallel to the contact face. Examples of such devices are disclosed in WO 2011/113823. With such an arrangement, the device can be temporarily secured in position at the injection site, for example using an adhesive on the contact face, or by using a strap or other apparatus, which can significantly improve user comfort during long injection durations.

One difficulty with known wearable devices is that a pre-filled syringe with a staked needle can no longer readily be used, and instead a path for flow of the medicament must be established between the medicament container and the needle without compromising the sterility of the medicament. Accordingly, such devices often require the user to perform one or more additional steps to prepare the device for delivery, which undesirably increases the complexity of operation. Furthermore, the use of specialised medicament containers may be required that cannot also be used in other devices.

Furthermore, in some cases, it is necessary or advantageous to supply a medicament to a user as two separate components, and to mix the components just prior to use.

For instance, some injectable medicaments, such as blood factors for the treatment of haemophilia and glucagon for the treatment of severe hypoglycaemia, have an unacceptably short shelf-life when in liquid form, and are therefore most commonly supplied in freeze-dried or lyophilised form as a solid powder. In the lyophilised form, the shelf life of the medicament is substantially extended. Prior to use, the medicament must be reconstituted by mixing with a suitable sterile diluent, such as water or saline. It would be desirable to provide devices that are capable of automatically mixing and subsequently delivering such medicaments.

Against this background, and from one aspect, the present invention resides in a medicament delivery device for delivery of medicament from a cartridge into an injection site through a cannula. The cartridge comprises a medicament chamber having an outlet, and a sealing element for closing the outlet. The device comprises a housing for receiving the cartridge, a drive mechanism comprising a drive element that is moveable with respect to the housing in a forward direction along a drive axis to expel the medicament from the device upon activation of the drive mechanism, and a connection arrangement comprising a hub and spring means for driving relative movement between the hub and the cartridge upon operation of an operating member of the device so as to switch the connection arrangement from an unconnected configuration in which the outlet is closed to a connected configuration in which the hub cooperates with the cartridge to open the outlet, thereby to establish a connection for fluid flow between the chamber and the cannula.

In this way, the medicament can remain sealed and sterile in the cartridge until just prior to use of the device. Then, the operating member can be operated to connect the medicament chamber to the cannula. By providing a spring means, the required relative movement between the hub and the cartridge can be driven automatically, thus allowing the connection step to be incorporated into another operating step of the device, such as removal of a shield or operation of a trigger button.

Furthermore, the provision of a hub for connection to the cartridge allows for flexibility in the positions of the cannula, the drive axis and the cartridge within the device. For example, the device may comprise a contact face for contact with the injection site for delivery of the medicament, and the drive axis may be substantially parallel to the contact face. In this way, a low-profile, wearable device with a relatively large contact face area can be provided.

Preferably, the hub is moveable with respect to the housing. Thus, the hub may be moveable with respect to the housing to switch the connection arrangement from the unconnected configuration to the connected configuration. For example, the spring means may bias the hub in a rearward direction along the drive axis. In another arrangement, the cartridge is moveable with respect to the housing to switch the connection arrangement from the unconnected configuration to the connected configuration. In this case, the spring means may bias the cartridge in the forward direction along the drive axis. The spring means preferably comprises a compression spring.

The device may comprise a control mechanism for holding the connection arrangement in the unconnected configuration and for allowing relative movement between the cartridge and the hub upon operation of the operating member to switch the connection arrangement to the connected configuration.

Preferably, a control piece is provided for controlling relative movement between the hub and the housing. The control piece may be releasable for movement with respect to the housing upon operation of the operating member. The spring means may act to bias the control piece for movement with respect to the housing. The control piece may be coupled to the hub for joint movement with respect to the housing.

Conveniently, movement of the control piece may be controlled by the device in order to effect switching of the connection mechanism. For example, the device may include a blocking formation for preventing movement of the control piece with respect to the housing. In this case, operation of the operating member may cause disengagement of the blocking formation from the control piece to allow movement of the control piece with respect to the housing. In one embodiment, the blocking formation is associated with the operating member.

The device may include a cannula holder that is moveable in an insertion direction with respect to the housing for extending the cannula into the injection site. In this case, when a blocking formation is provided, the blocking formation may be associated with the cannula holder, and movement of the cannula holder in the insertion direction may cause disengagement of the blocking formation from the control piece.

When a cannula holder is provided, the insertion direction of the cannula holder is preferably non-parallel to the drive axis. For example, the insertion direction may be perpendicular to the drive axis. In this way, the device can be positioned with the contact face against the injection site, and then insertion of the cannula can take place without further movement of the device. The device may include a flexible tube for providing a fluid connection between the hub and the cannula holder.

An insertion spring may be provided for driving movement of the cannula holder in the insertion direction. The device may include a latch mechanism for latching the cannula holder in a retracted position and for releasing the cannula holder from the retracted position for movement of the cannula holder in the insertion direction. For example, when a control piece is provided, the cannula holder may be latched to the control piece when in the retracted position. To this end, the cannula holder may comprise a latch member that is engageable with the control piece.

The cannula holder may be coupled to the control piece for movement with respect to the housing along the drive axis. For example, in one embodiment, the cannula holder is first displaced with the control piece along the drive axis in one operating stage of the device, and then released from the control piece for insertion of the cannula in a subsequent operating stage of the device. As will be explained below, this arrangement can be useful to accommodate movement of the outlet end of the cartridge during a mixing stroke in embodiments of the invention that are arranged to mix two substances prior to delivery of the mixture.

Release of the latch mechanism may be caused by relative movement between the control piece and the cannula holder. For instance, the latch mechanism may be arranged to release the cannula holder upon forward movement of the control piece with respect to the cannula holder. In this case, the control piece may comprise a slot, and the slot may be shaped to release the latch member from the slot upon forward movement of the control piece.

Release of the latch mechanism may be caused by operation of the operating member, such that insertion of the cannula is associated with switching of the connection arrangement. For example, the latch mechanism may comprise a latch release member associated with the operating member for releasing the cannula holder upon movement of the operating member relative to the housing. Where the device includes a trigger component for activation of the drive mechanism that is separate to the operating member, release of the latch mechanism may be caused by operation of the trigger component.

Guide means may be provided for guiding movement of the cannula holder in the insertion direction. The guide means may comprise a guide formation, which may have a fixed position with respect to the housing. Alternatively, the guide formation may be moveable in the forward direction with respect to the housing, for example when the cannula holder is coupled to a control piece that moves with respect to the housing during an operating step of the device. In this case, the device may comprise a catch arrangement for latching the guide formation in a forward position with respect to the housing to prevent subsequent movement of the cannula holder along the drive axis.

Preferably, the hub is arranged for engagement with a coupling element disposed at an outlet end of the cartridge. Thus, with a suitably designed hub, the device may be suitable for use with cartridges that can also be used in multiple other types of medicament delivery device.

The hub may be engageable with the coupling element in a first attachment position in the unconnected configuration of the connection arrangement and in a second attachment position in the connected configuration of the connection arrangement. The hub may comprise at least one clip for engagement with one or more respective engagement formations of the coupling element.

Preferably, the hub comprises a sealing element release member for cooperation with the sealing element of the cartridge to open the outlet when the connection arrangement is switched to the connected configuration. For example, the sealing element may be a pierceable septum, and the sealing element release member may comprise a piercing member for piercing the sealing element.

To maintain the sterility of the sealing element release member and the fluid flow path from the hub to the cannula, when the connection arrangement is in the unconnected configuration, a seal arrangement may be provided. The seal arrangement may form a seal with the coupling element to enclose a tip of the sealing element release member in an enclosed chamber when the connection arrangement is in the unconnected state. For example, the seal arrangement may form a seal around the sealing element release member. The enclosed chamber may be disposed on a forward side of the sealing element.

The device may be arranged for the delivery of a single medicament substance from a cartridge having a single chamber. However, embodiments of the invention are arranged for mixing two substances within the device before delivery of the mixed substance. Thus, the device may be suitable for use with a cartridge comprising a first container having a first chamber for a first substance, a second container telescopically received in the first container and having a second chamber for a second substance, valve means for closing a forward end of the second chamber and a rearward end of the first chamber, and stopper means for closing a rearward end of the second chamber. The device may comprise a mixing element for causing displacement of the second substance into the first chamber through the valve means in a mixing stroke of the device. Preferably, the mixing stroke of the device is performed before switching of the connection arrangement to the connected state.

The mixing element may comprise a plunger that is moveable in the forward direction during the mixing stroke for cooperation with the stopper means. A mixing spring may be provided for biasing the mixing element in the forward direction. The device may include a latch mechanism for holding the mixing element in an initial position and for releasing the mixing element for movement upon release of the latch mechanism to start the mixing stroke of the device. The latch mechanism may be releasable upon removal of a user-removable component, such as a shield for shielding the cannula.

The drive element of the drive mechanism is preferably arranged to move to the second container of the cartridge in the forward direction upon operation of the drive mechanism to expel the mixed first and second substances from the first chamber. A clamp arrangement may be provided for securing the drive element to the second container.

The drive element may be arranged to hold the second container in an initial position with respect to the housing during the mixing stroke, such that the first container moves in the forward direction during the mixing stroke. In this case, when a cannula holder is provided, forward movement of the first container during the mixing stroke may cause movement of the cannula holder along the drive axis to a forward position.

A locking arrangement may be provided for preventing switching of the connection arrangement to the connected state during the mixing stroke. The locking arrangement may be arranged to couple the hub and the first container for joint movement with respect to the housing during the mixing stroke. The locking arrangement may be releasable to allow relative movement of the hub and the first container at the end of the mixing stroke. For example, the locking arrangement may comprise a locking element and a recess for receiving the locking element at the end of the mixing stroke.

The drive mechanism may comprise a drive member that is rotatable with respect to the housing and driving means for driving rotation of the drive member. For example, the driving means may comprise a power spring. With such an arrangement, a relatively high force can be applied by the drive mechanism, which can be particularly useful for the delivery of relatively viscous medicaments or for the delivery of large volumes. A transmission member, such as a flexible chain, may be provided for transferring force from the drive member to the drive element.

In another arrangement, the drive element is biased for movement in the forward direction, for example by a drive spring that may be disposed along the drive axis.

The operating member may comprise a shield for shielding the cannula. The shield may be moveable to expose the cannula and to cause switching of the connection arrangement into the connected state. In this way, switching of the connection arrangement can be performed automatically during operation of the device when the shield is moved to expose the cannula, so that no additional user action is required. Preferably, the shield is removable from the housing to expose the cannula.

The device may include a trigger component that is moveable with respect to the housing to activate the drive mechanism. In this case, the trigger component may comprise the operating member, such that switching of the connection arrangement can be performed automatically when the user operates the trigger component to activate the drive mechanism, again with no additional user action being required.

The trigger component may be moveable from a first position to a second position to activate the drive mechanism. A trigger element may be provided for blocking operation of the drive mechanism, in which case movement of the trigger component to the second position may cause movement of the trigger element to release the drive mechanism. For example, when the drive mechanism comprises a rotatable drive member, the trigger element may engage with a suitable formation, such as a tooth, of the drive member to block rotation of the drive member. The trigger element may be biased to disengage from the drive mechanism.

A lock member may be associated with the trigger component for holding the trigger element in engagement with a drive member of the drive mechanism. In this case, movement of the trigger component to the second position may cause disengagement of the trigger element from the drive member, for example by moving the lock member clear of the trigger component.

In another arrangement, the device includes a latch arrangement for latching the drive element in an initial position with respect to the housing, and movement of the trigger component to the second position causes release of the latch arrangement to activate the drive mechanism. A latch release formation may be associated with the trigger component and arranged for cooperation with a latch member of the drive element to release the latch arrangement upon movement of the trigger component to the second position.

When the device includes a cannula holder, movement of the cannula holder in an insertion direction is preferably triggered by movement of the trigger component. For example, the trigger component may be moveable from a first position to an intermediate position to cause movement of the cannula holder in an insertion direction to insert the cannula and from the intermediate position to the second position to activate the drive mechanism.

For example, in one arrangement, movement of the cannula in the insertion direction is triggered by forward movement of the cartridge. Thus the device may include a cartridge spring for biasing the cartridge in the forward direction with respect to the housing, and a latch arrangement for holding the cartridge in an initial position when the trigger component is in the first position and for releasing the cartridge for movement in the forward direction to cause insertion of the cannula upon movement of the trigger component to the intermediate position. A carrier may be provided for receiving the cartridge, and the cartridge spring may act upon the carrier to bias the carrier and the cartridge in the forward direction.

The device may include a cannula, which is preferably a hypodermic needle. The device may include a cartridge comprising a medicament chamber having an outlet and a sealing element for closing the outlet.

From another aspect of the invention, a medicament delivery device is provided for delivery of medicament from a cartridge into an injection site through a cannula. The cartridge comprises a medicament chamber having an outlet, and a sealing element for closing the outlet. The device comprises a housing for receiving the cartridge, a cannula holder that is moveable in an insertion direction for extending the cannula into the injection site, a drive mechanism for expelling the medicament from the device upon activation of the drive mechanism, and a connection arrangement that is switchable from an unconnected configuration in which the outlet is closed to a connected configuration in which a fluid flow path is established between the chamber and the cannula. The device includes a removable shield for shielding the cannula, and a trigger component that is operable to activate the drive mechanism. Movement of the cannula holder in the insertion direction and switching of the connection arrangement to the connected configuration are each triggered either by removal of the shield or by operation of the trigger component. In this way, only two user interactions with the device are required.

Optionally, the device may be operable to perform a mixing stroke to mix two substances in the device before activation of the drive mechanism. In this case, the mixing stroke is also triggered either by removal of the shield or by operation of the trigger component.

A further aspect of the invention resides in a medicament delivery device for delivery of medicament from a cartridge into an injection site through a cannula, the cartridge comprising a medicament chamber having an outlet, and a sealing element for closing the outlet, the device comprising a housing for receiving the cartridge, a drive mechanism comprising a drive element that is moveable with respect to the housing to expel the medicament from the device upon activation of the drive mechanism, a cannula insertion arrangement operable to move the cannula in an insertion direction, and a connection arrangement comprising a hub and means for driving relative movement between the hub and the cartridge along a connection axis of the device to switch the connection arrangement from an unconnected configuration in which the outlet is closed to a connected configuration in which the hub cooperates with the cartridge to open the outlet, thereby to establish a connection for fluid flow between the chamber and the cannula. The insertion direction is non-coaxial with the connection axis. Preferably, the insertion direction is inclined with respect to the connection axis, and more preferably the insertion direction is perpendicular to the connection axis. In this way, a low-profile device can be provided. Medicaments, including pharmaceutical compositions, contemplated for use in the delivery device may comprise small molecules, vaccines, live or attenuated cells, oligonucleotides, DNA, peptides, antibodies, and recombinant or naturally occurring proteins, whether human or animal, useful for prophylactic, therapeutic or diagnostic application. The active ingredient can be natural, synthetic, semi-synthetic or derivatives thereof. A wide range of active ingredients are contemplated. These include, for example, hormones, cytokines, hematopoietic factors, growth factors, antiobesity factors, trophic factors, antiinflammatory factors, and enzymes. The pharmaceutical compositions also may include, but are not limited to, insulin, gastrin, prolactin, human growth hormone (hGH), adrenocorticotropic hormone (ACTH), thyroid stimulating hormone (TSH), luteinizing hormone (LH), follicle stimulating hormone (FSH), human parathyroid hormone (PTH), glucagon, glucagons-like peptide 1 (GLP-1), glucagons-like peptide 2 (GLP-2), insulin-like growth factors (IGFs) such as insulin growth factor I (IGF I), insulin growth factor II (IGF II), growth hormone-releasing factor (GRF), human chorionic gonadotropin (HCG), gonadotropin-releasing hormone, motilin, interferons (alpha, beta, gamma), interleukins (e.g., IL-1, IL-2, IL-4, IL-5, IL-6, IL-9, IL-11, IL-12, IL-13, IL-15, IL-16, IL-17, IL-18, IL-20 or IL-21), interleukin-1 receptor antagonists (IL-Ira), tumor necrosis factor (TNF), tumor necrosis factor-binding protein (TNF-bp), CD40L, CD30L, erythropoietin (EPO), plasminogen activator inhibitor 1, plasminogen activator inhibitor 2, von Willebrandt factor, thrombopoietin, angiopoietin, granulocyte-colony stimulating factor (G-CSF), stem cell factor (SCF), leptin (OB protein), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), transforming growth factors, epidermal growth factor (EGF), vascular endothelial growth factor (VEGF), macrophage colony stimulating factor (M-CSF), granulocyte macrophage colony stimulating factor (GM-CSF), megakaryocyte derived growth factor (MGDF), keratinocyte growth factor (KGF), platelet-derived growth factor (PGDF), novel erythropoiesis stimulating protein (NESP), bone morphogenetic protein (BMP), superoxide dismutase (SOD), tissue plasminogen activator (TPA), pro-urokinase, urokinase, streptokinase, kallikrein, a protease inhibitor e.g. aprotinin, an enzyme such as asparaginase, arginase, arginine deaminase, adenosine deaminase, ribonuclease, catalase, uricase, bilirubin oxidase, trypsin, papain, alkaline phosphatase, glucoronidase, purine nucleoside phosphorylase or batroxobin, an opioid, e.g. endorphins, enkephalins or non-natural opioids, a neuropeptide, neuropeptide Y, calcitonin, cholecystokinins, corticotrophin-releasing factor, vasopressin, oxytocin, antidiuretic hormones, thyrotropin releasing hormone, relaxin, peptideYY, pancreastic polypeptide, CART (cocaine and amphetamine regulated transcript), a CART related peptide, perilipin, melanocortins (melanocyte-stimulating hormones) such as MSH, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins, and human antibodies and humanized antibodies, and other pharmaceutical compositions suitable for administration with the delivery devices described herein. The term proteins, as used herein, includes peptides, polypeptides, consensus molecules, analogs, derivatives or combinations thereof.

The pharmaceutical compositions also may include therapeutic and pharmaceutic agents such as, but not limited to: antiproliferative/antimitotic agents including natural products such as vinca alkaloids (i.e. vinblastine, vincristine, and vinorelbine), paclitaxel, epipidopodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoaglants (heparin, synthetic heparin salts and other inhibitors of thrombin); fibrinolytic agents (such as tissue plasminogen activator, streptokinase and urokinase); antiplatelet (aspirin, dipyridamole, ticlopidine, clopidogrel, abciximab); antimigratory; antisecretory (breveldin); antiinflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); nitric oxide donors; anti-sense olgio nucleotides and combinations thereof.

The pharmaceutical compositions include any extended half-life variants of active ingredients contained therein or analogues thereof. Thus, the active ingredients can be any long acting variants of the active ingredient listed herein or analogues thereof. In some embodiments, the active ingredient includes any extended half-life or long acting variants of hGH, insulin, glucagon, glucagons-like peptide 1 (GLP-1), glucagons-like peptide 2 (GLP-2), insulin-like growth factors (IGFs). In some embodiments, the active ingredient is an extended half-life or long acting variant of hGH. Examples of extended half-life or long acting variants of hGH include, but are not limited to LB03002, NNC126-0883, NNC0195-0092, MOD-4023, ACP-001, Albutropin, somavaratan (VRS-317), and profuse GH.

In a still further aspect of the invention, a medicament delivery device for delivery of medicament from a cartridge into an injection site through a cannula is provided. The cartridge comprises a medicament chamber having an outlet, and a sealing element for closing the outlet and the device comprises a housing for receiving the cartridge, a drive mechanism comprising a drive element that is moveable with respect to the housing to expel the medicament from the device upon activation of the drive mechanism, a cannula insertion arrangement operable to move the cannula in an insertion direction, and a hub for connection to the cartridge. The hub and the cartridge are moveable relative to one another to operate the needle insertion arrangement and to switch the connection arrangement from an unconnected configuration in which the outlet is closed to a connected configuration in which the hub cooperates with the cartridge to open the outlet, thereby to establish a connection for fluid flow between the chamber and the cannula.

Another aspect of this invention is directed to one or more of the medicaments, including one or more pharmaceutical compositions, as described above for subcutaneous injection or infusion, disposed within the medicament delivery devices described herein for the delivery of the medicament from a cartridge into an injection site through a cannula. Additionally, this invention contemplates methods of administering one or more of the medicaments, including pharmaceutical compositions, to patients with conditions susceptible to treatment with the medicaments, as well as methods of treating those conditions, by delivering the appropriate medicament using the delivery devices described herein.

Preferred and/or optional features of each embodiment and aspect of the invention may also be used alone or in appropriate combinations not explicitly described herein Embodiments of the present invention will now be described, by way of example only, with reference to the accompanying drawings, in which like reference numerals are used for like features, and in which:

FIG. 1 is an isometric view of a medicament delivery device according to a first embodiment of the present invention, when in an initial state;

FIGS. 2(a) and 2(b) are top and isometric views, respectively, of the delivery device of FIG. 1 when in the initial state, with an upper housing part omitted for clarity;

FIGS. 3(a) and 3(b) are cross-sectional views of the delivery device of FIG. 1 along a horizontal plane and a vertical plane, respectively;

Figure 1:
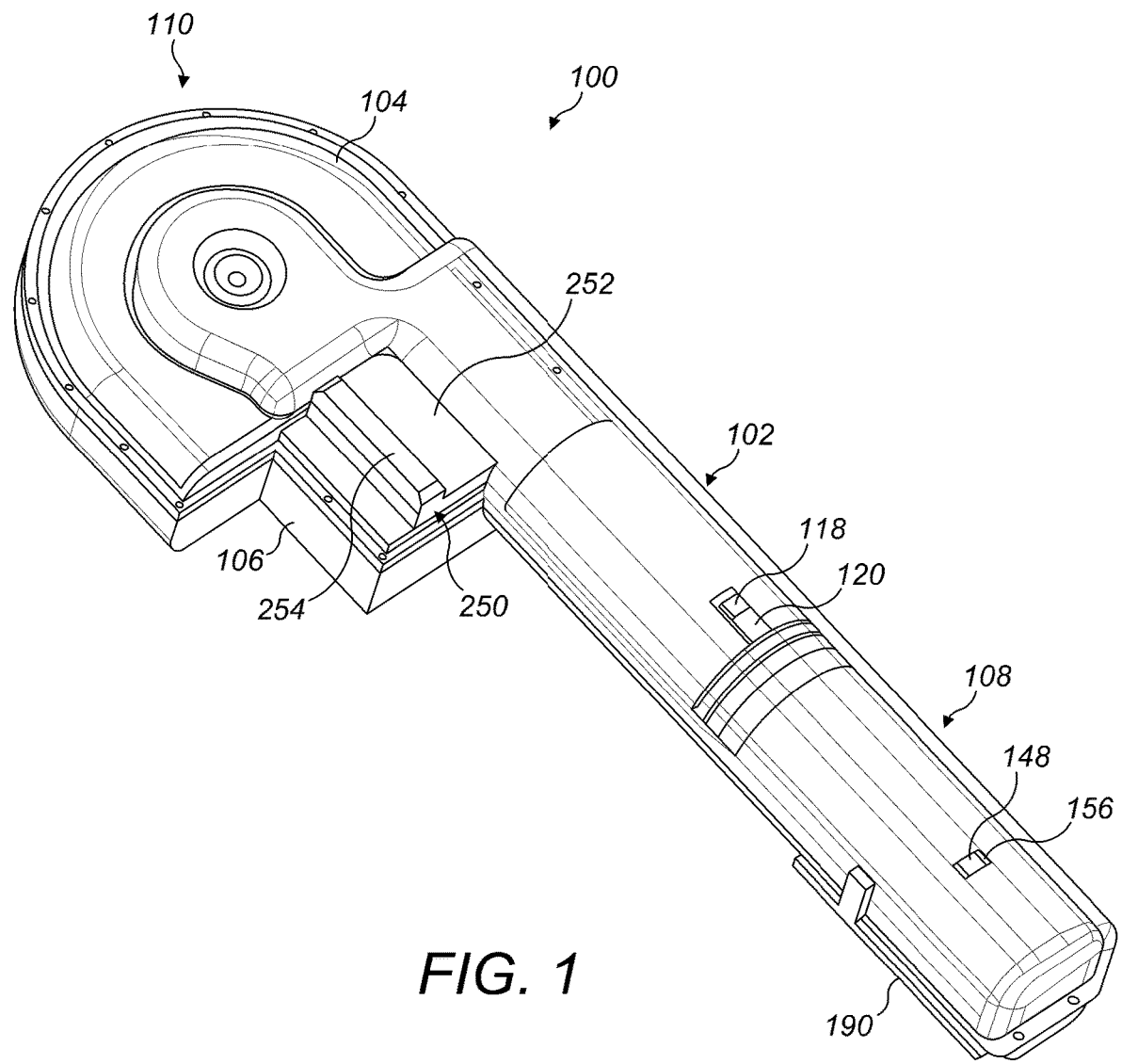
Figure 11A:
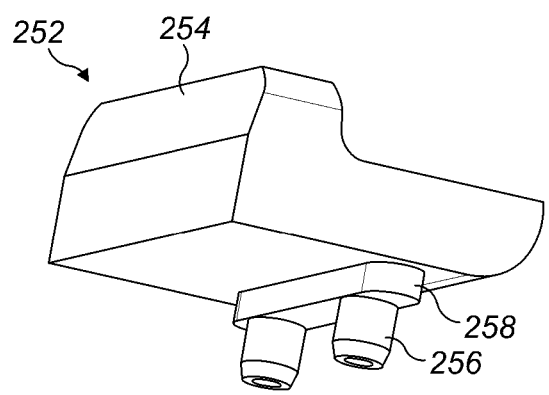
Figure 11B:
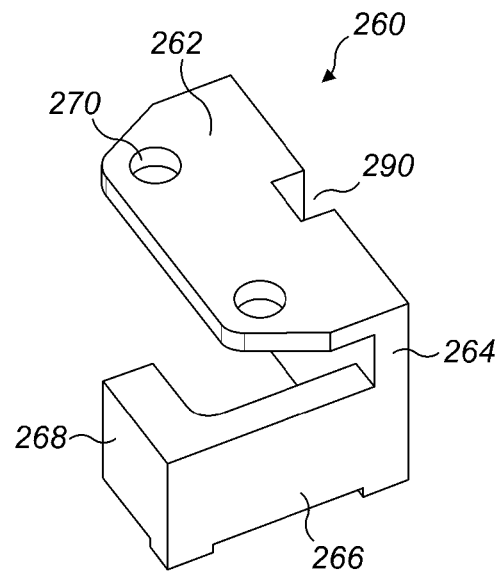
Figure 12:
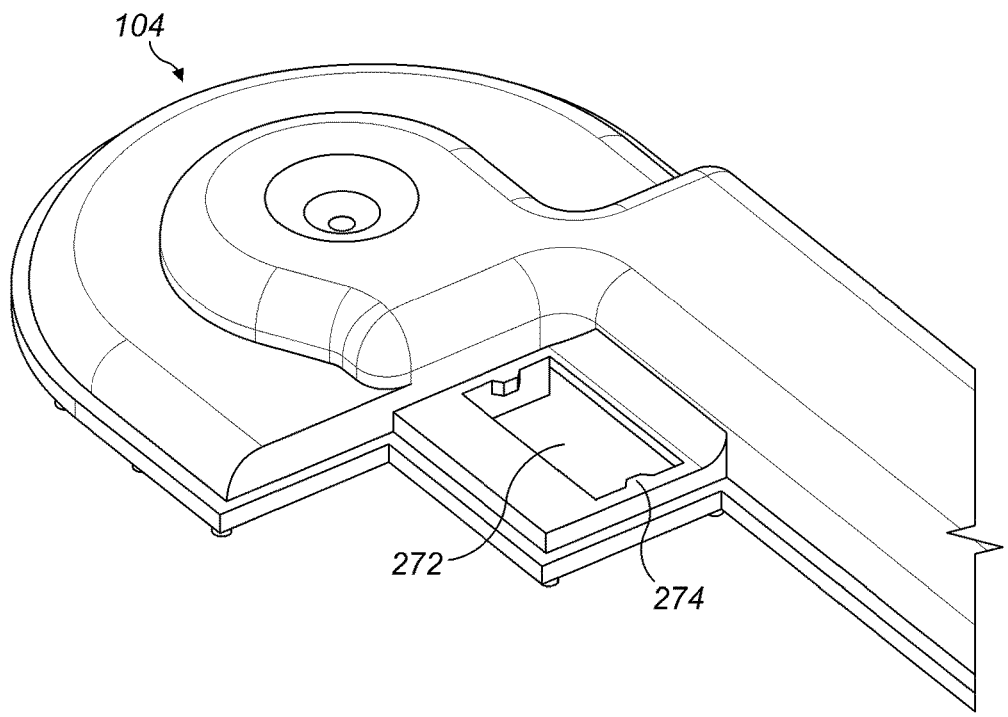
Figure 13A:
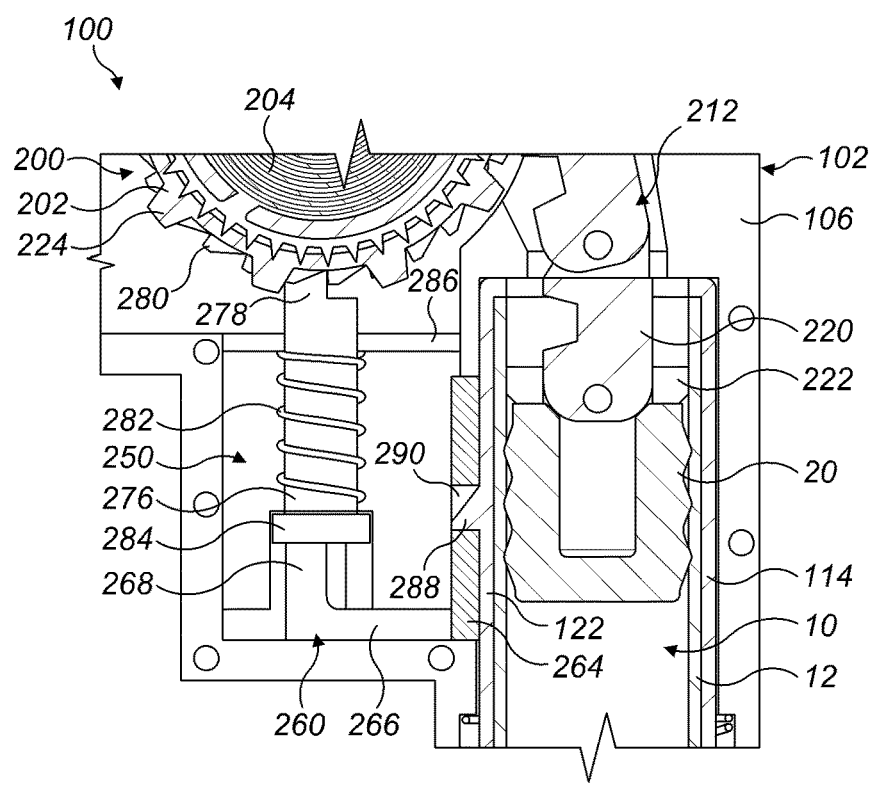
Figure 13B:
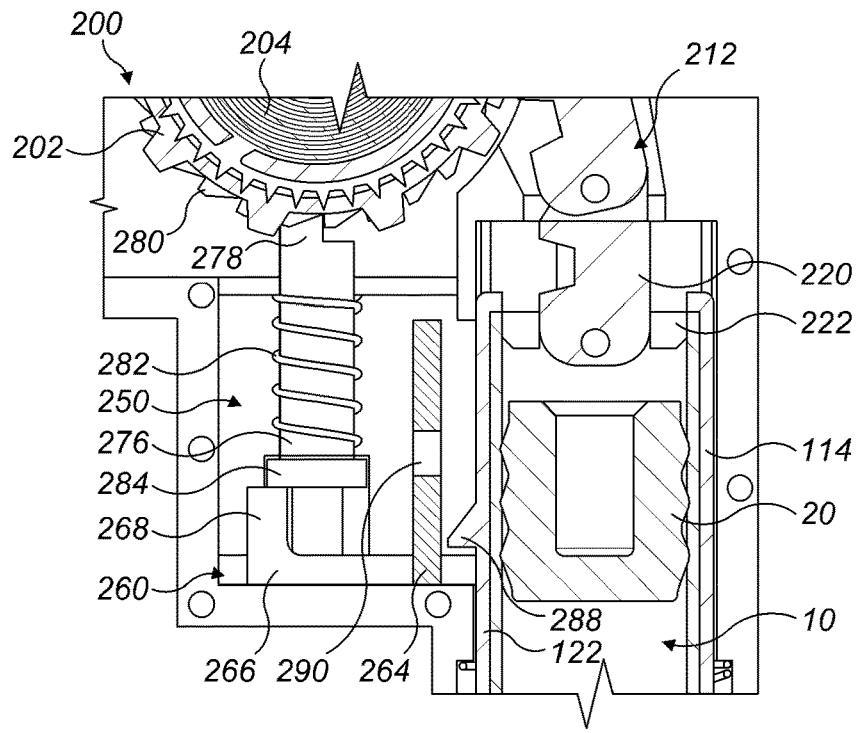
Figure 13C:
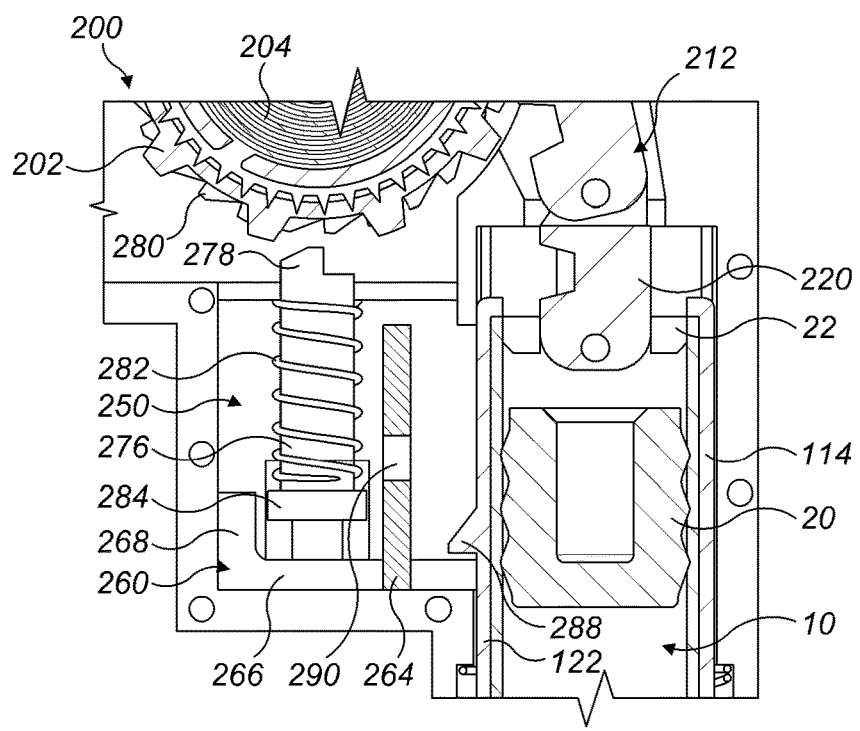
Figure 16:
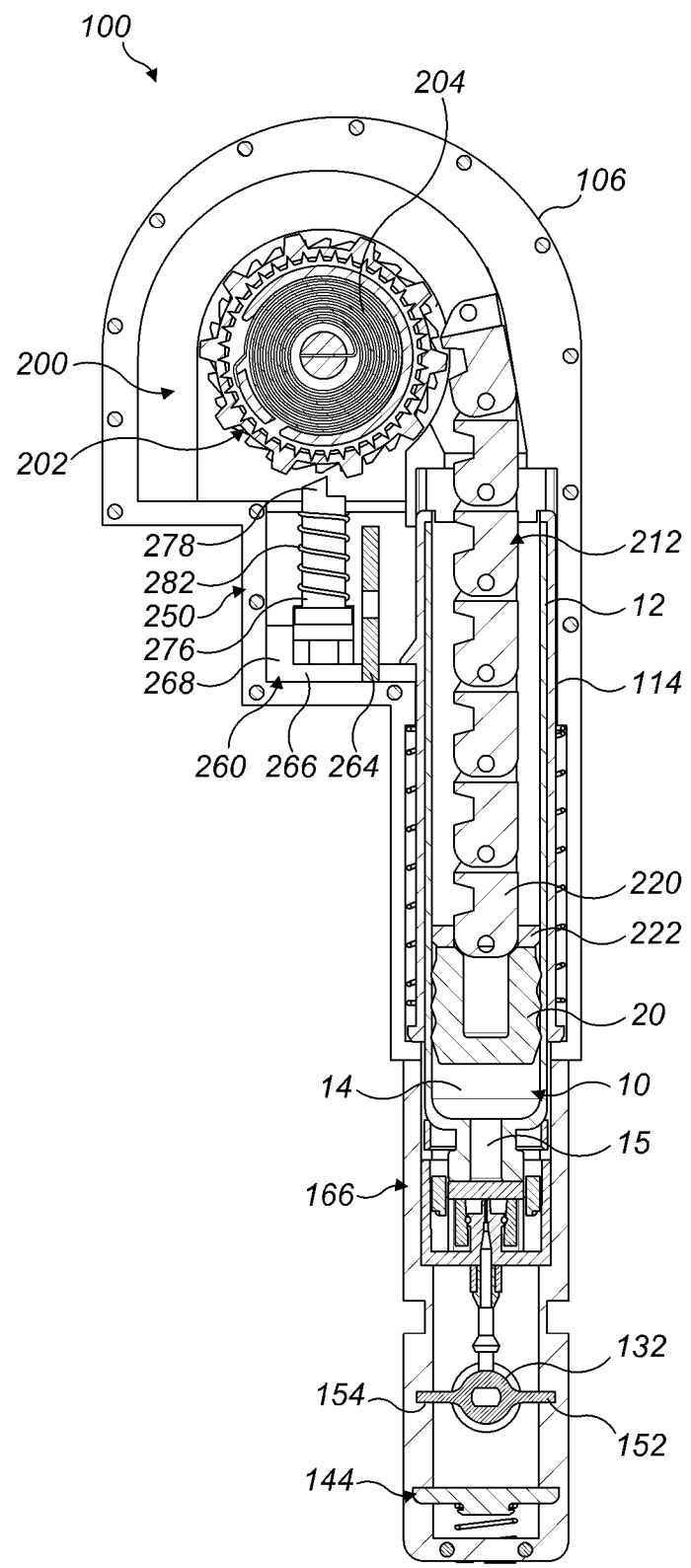
Figure 17A:
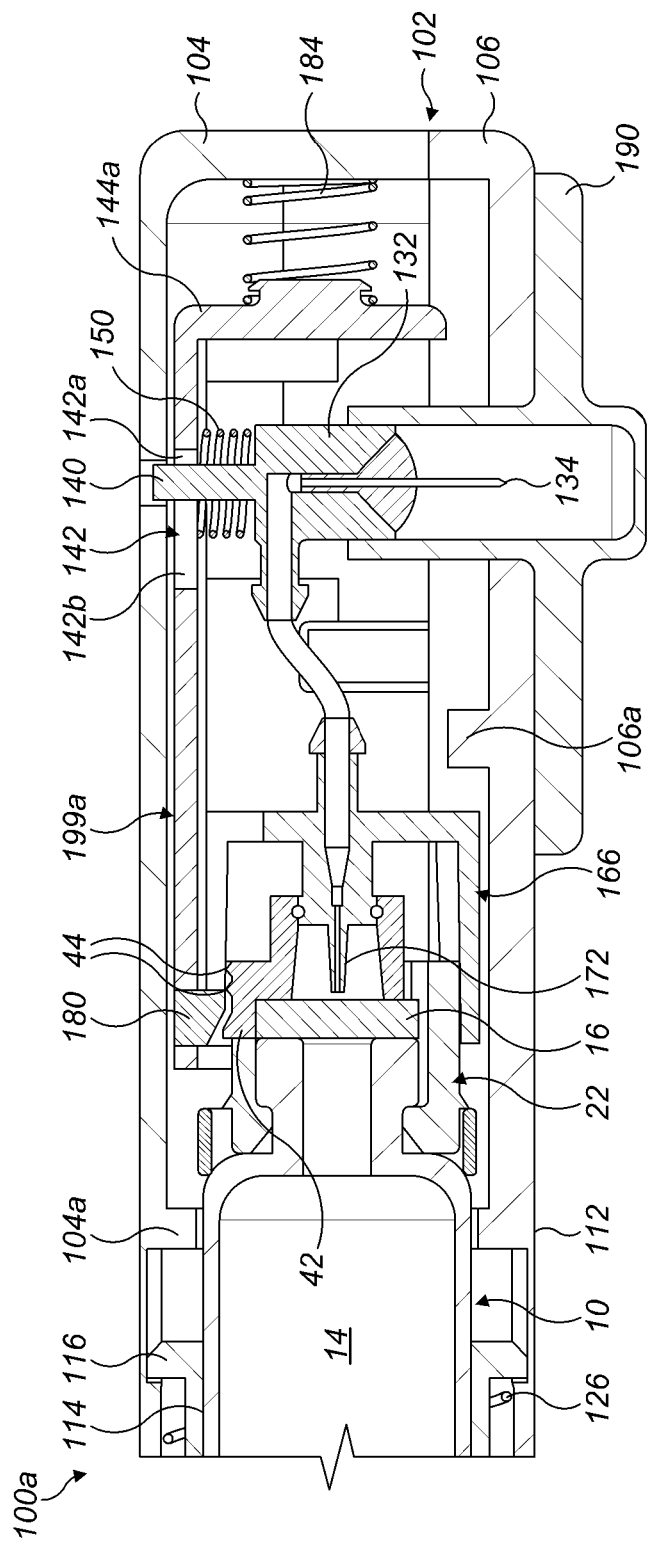
Figure 20:
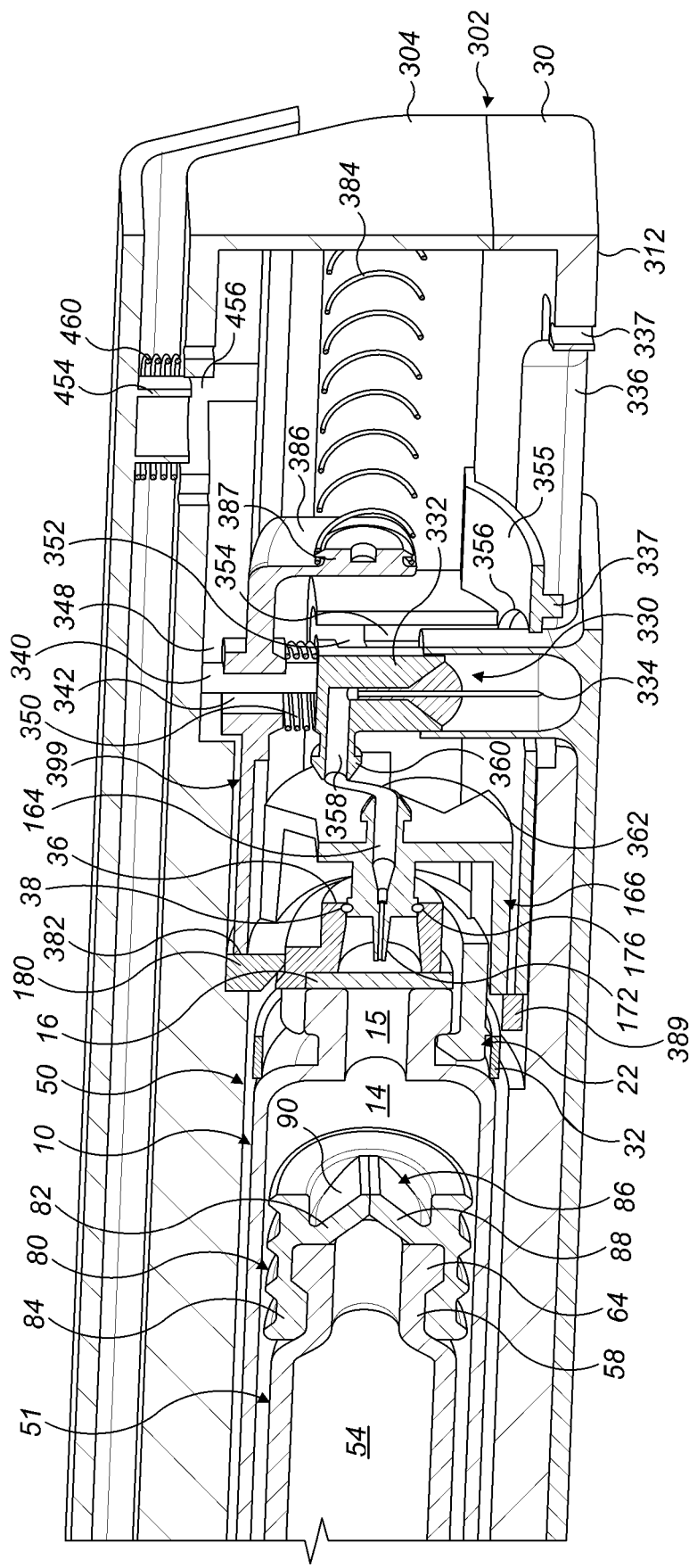
Figure 24:
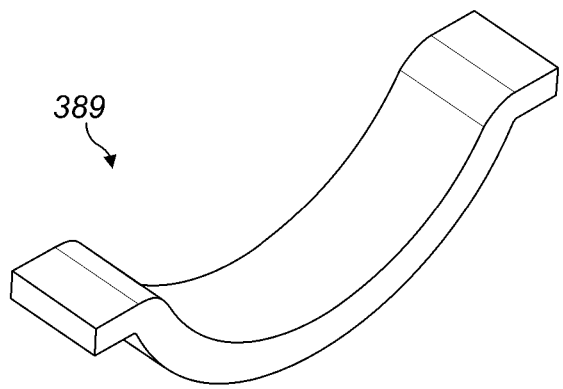
Figure 25:
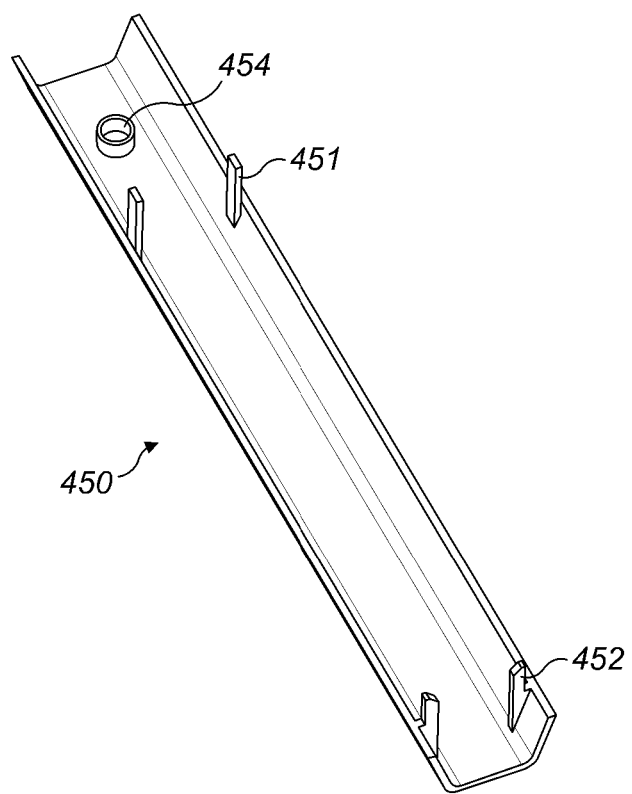
Figure 26:
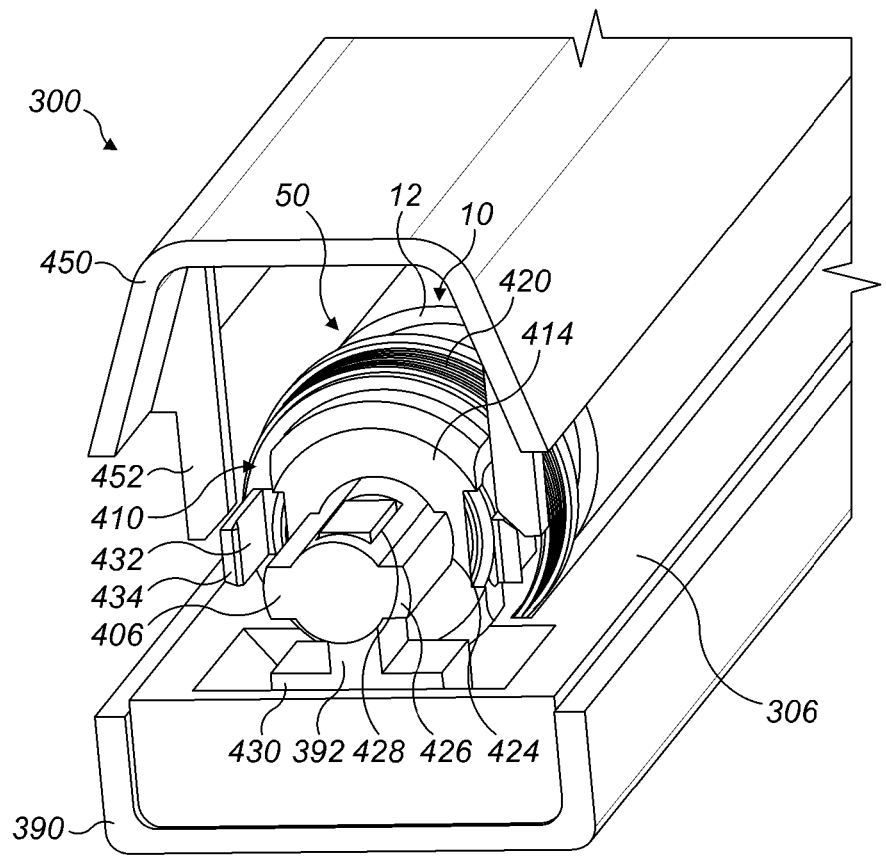
Figure 27:
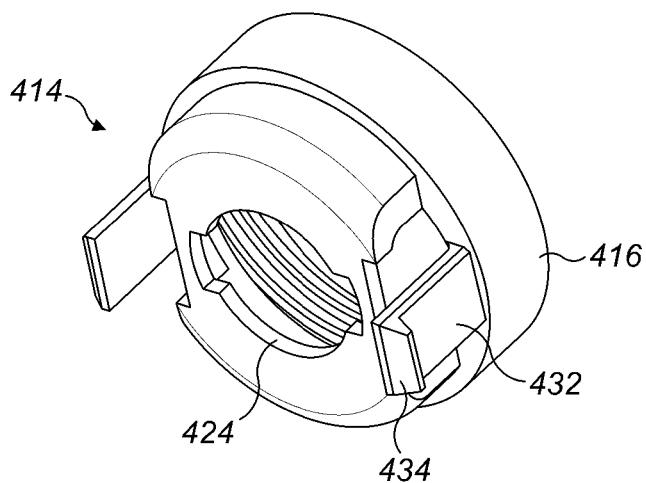
Figure 28:
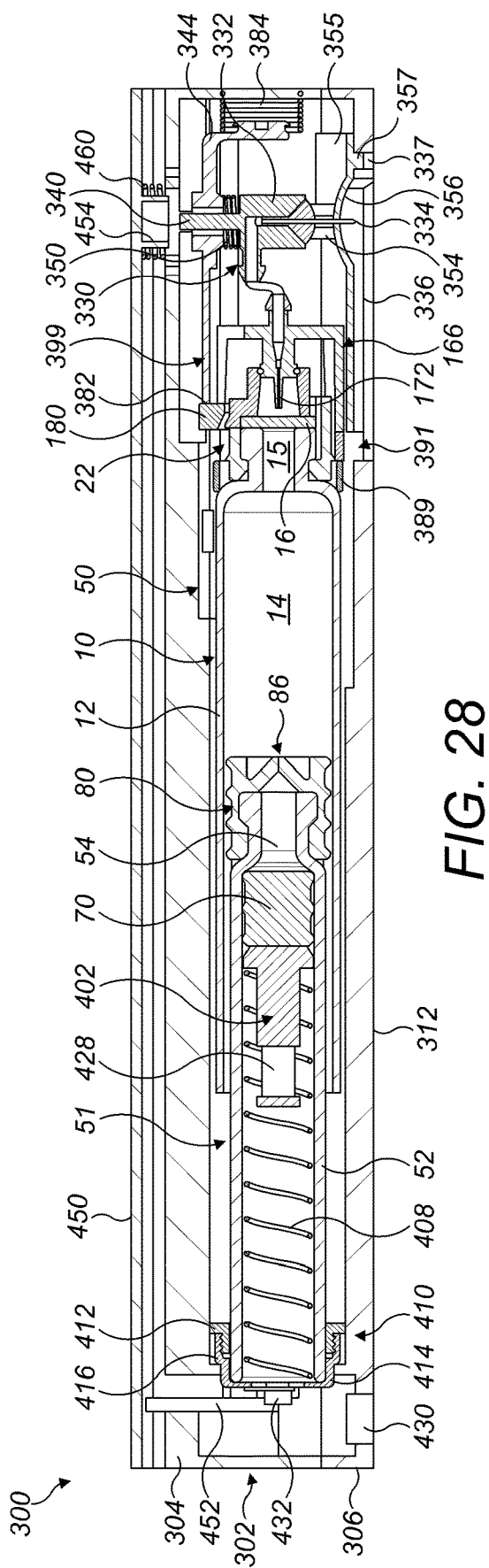
Figure 29:
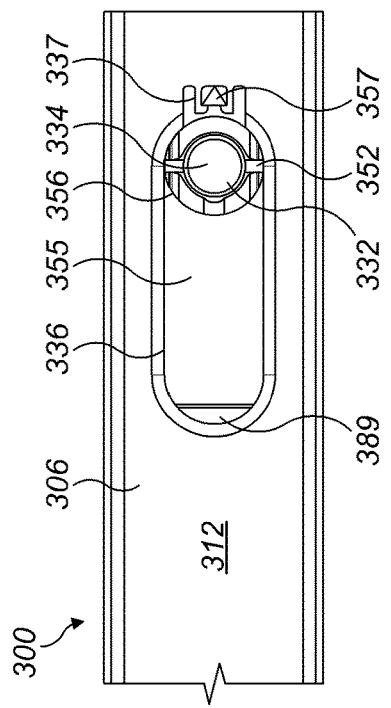
Figure 30A:
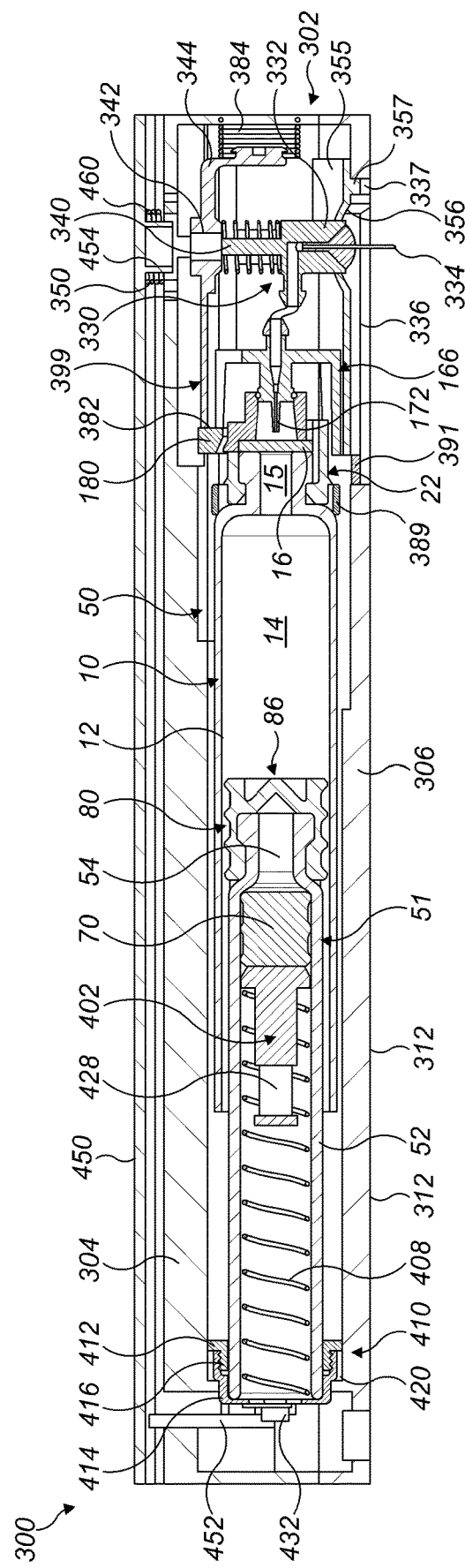
Figure 30B:
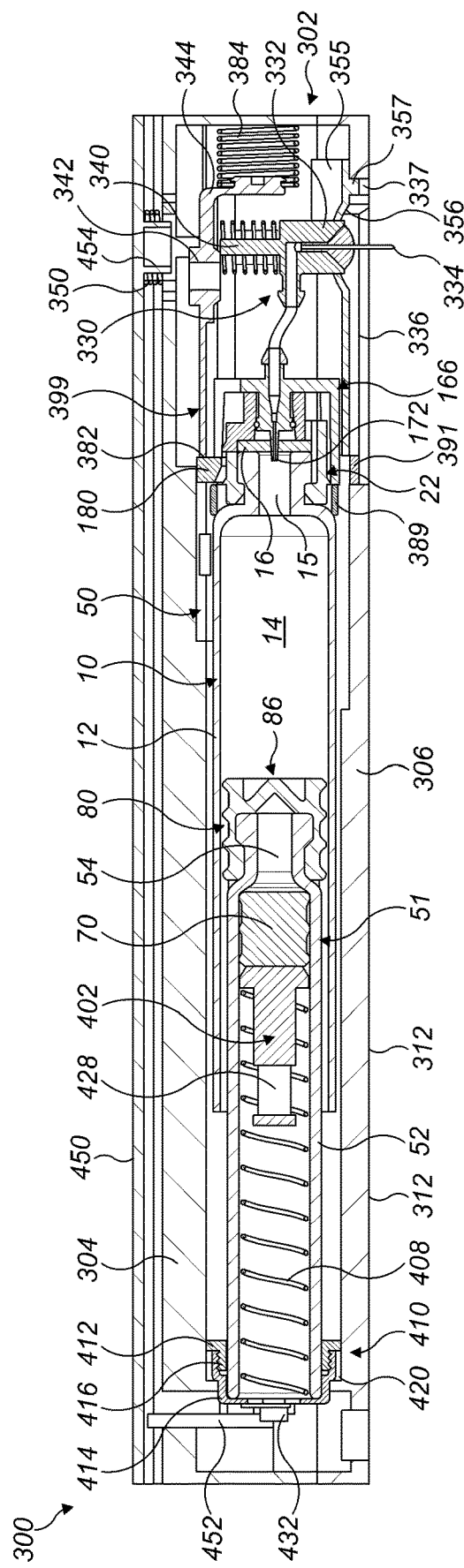
Figure 31:
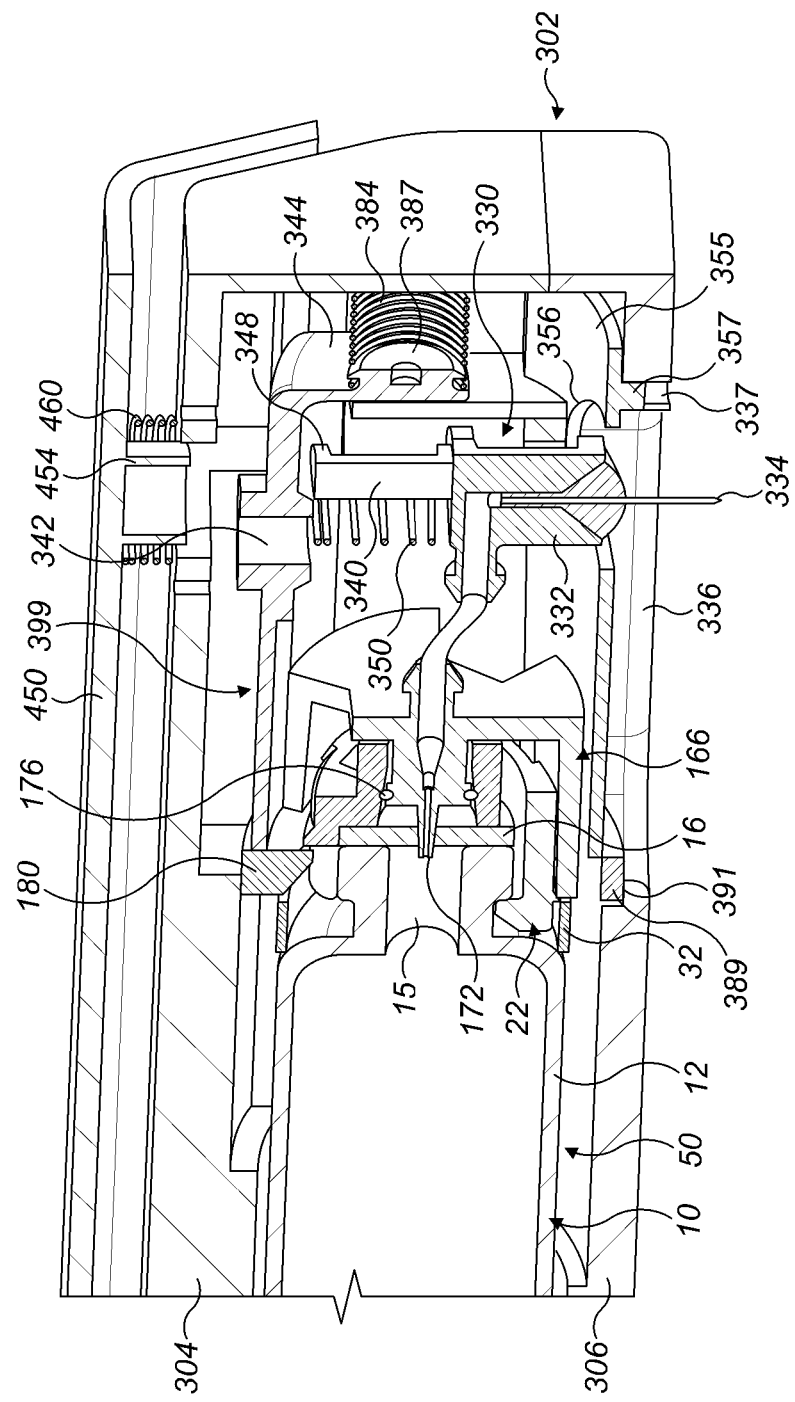
Figure 32:
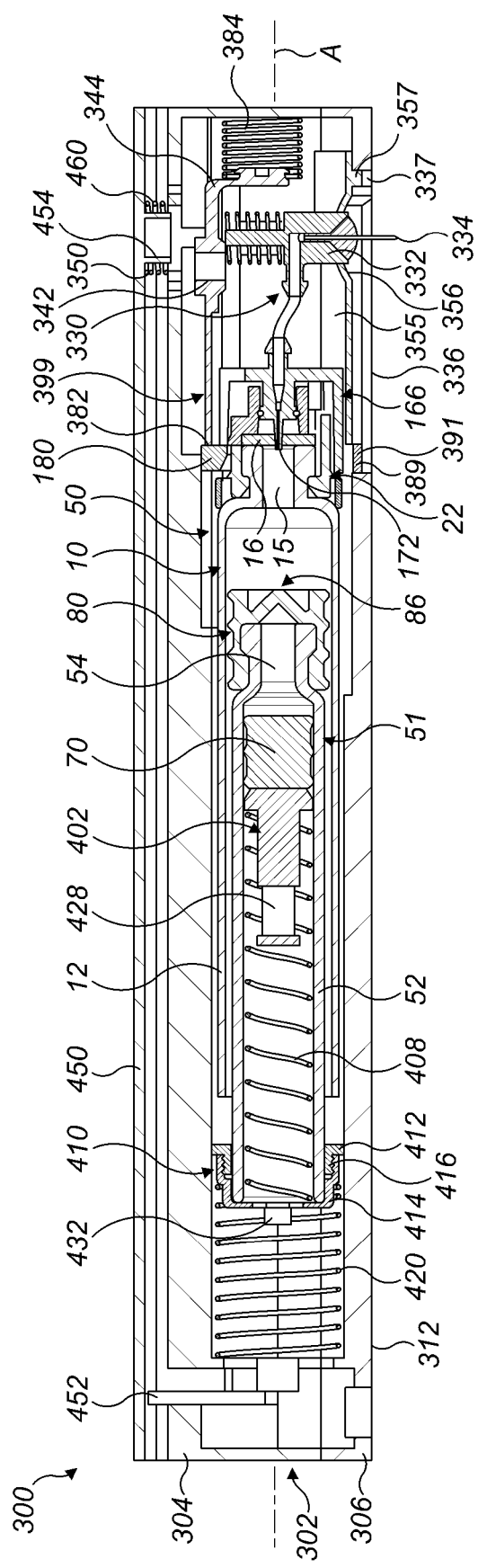

FIGS. 11(a) and 11(b) are isometric views of parts of the trigger assembly;

FIG. 12 is an isometric view of part of the upper housing part of the device of FIG. 1;

FIGS. 13(a), 13(b) and 13(c) are part-sectional views of part of the device of FIG. 1 before operation of the trigger assembly and in first and second operational positions of the trigger assembly, respectively;

FIGS. 14(a) and 14(b) are top views of part of the device of FIG. 1 before operation of the trigger assembly and in the first operational position of the trigger assembly; respectively, corresponding to FIGS. 13(a) and 13(b);

FIGS. 15(a) and 15(b) are side views of part of the device of FIG. 1 before operation of the trigger assembly and in the first operational position of the trigger assembly; respectively, corresponding to FIGS. 13(a) and 13(b);

FIG. 16 is a cross-sectional view of the device of FIG. 1 after delivery of the medicament;

FIGS. 17(a), (b) and (c) are cross-sectional views of part of a variant of the device of FIG. 1 in an initial state, after removal of the shield component and after operation of the trigger assembly, respectively;

FIG. 18 is an isometric view of a medicament delivery device according to a second embodiment of the present invention, when in an initial state;

FIG. 19 is a cross-sectional view of the device of FIG. 18 when in the initial state;

FIG. 20 is a cut-away isometric view of a forward end part the device of FIG. 18 when in the initial state;

FIG. 21 is an isometric view of a needle holder of the device of FIG. 18;

FIG. 22 is an isometric view of a control piece of the device of FIG. 18;

FIGS. 23(a) and (b) are isometric views of part of a carriage piece of the device of FIG. 18;

FIG. 24 is an isometric view of a locking collar of the device of FIG. 18;

FIG. 25 is an isometric view of a trigger button of the device of FIG. 18;

FIG. 26 is an isometric view of a rearward end part of the device of FIG. 18 when in the initial state, with an upper housing part omitted for clarity;

FIG. 27 is an isometric view of a delivery drive element of the device of FIG. 18;

FIG. 28 is a cross-sectional view of the device of FIG. 18 after removal of a shield component;

FIG. 29 is a bottom view of part of the device of FIG. 18 after removal of the shield component;

FIGS. 30(a) and (b) are cross-sectional views of the device of FIG. 18 in successive operational stages;

FIG. 31 is a cut-away isometric view of part of the device of FIG. 18 in the operational stage shown in FIG. 30(b); and FIG. 32 is a cross-sectional view of the device of FIG. 18 in a further operational stage.

Throughout this description, terms such as "top", "bottom", "upper" and "lower" are used with reference to the orientation of the devices as shown in FIGS. 1 and 18, although it will be understood that the device could be disposed in any suitable orientation in use.

FIGS. 1 to 3 show a medicament delivery device 100 according to a first embodiment of the invention. The device 100 comprises a housing 102 having an upper housing part 104 and a lower housing part 106. The housing 102 is shaped to define an elongate portion 108 that extends from an enlarged portion 110. Referring to FIG. 2, in which the upper housing part 104 is omitted for clarity, and to FIG. 3, the elongate portion extends along a drive axis A of the device 100 and houses a cartridge-type medicament container 10, and a needle assembly 130 is disposed at a forward end of the elongate portion 108, remote from the enlarged portion 110. The enlarged portion 110 houses a drive mechanism 200 and a trigger assembly 250.

Figure 3A:
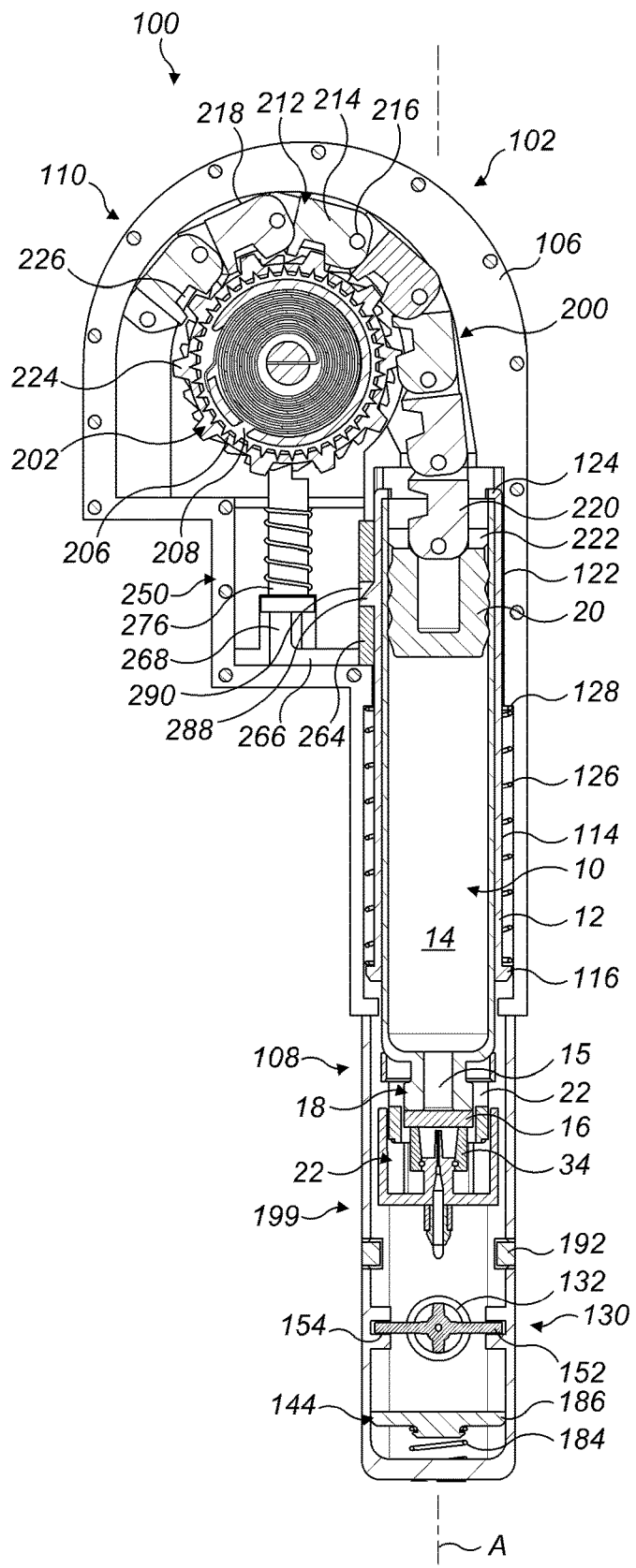
Figure 3B:
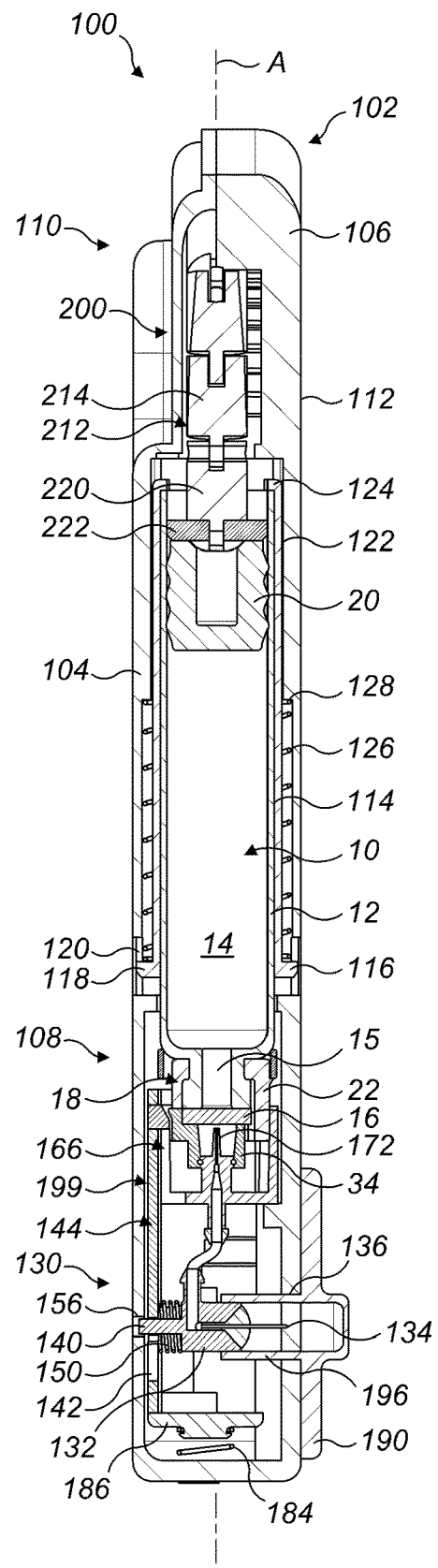

Referring to FIG. 3(b), the bottom of the lower housing part 106 provides a contact face 112 of the device 100. In use, the contact face 112 is placed against the skin of the patient, with the end region of the elongate portion 108 of the housing 102 over the desired injection site.

Figure 4:
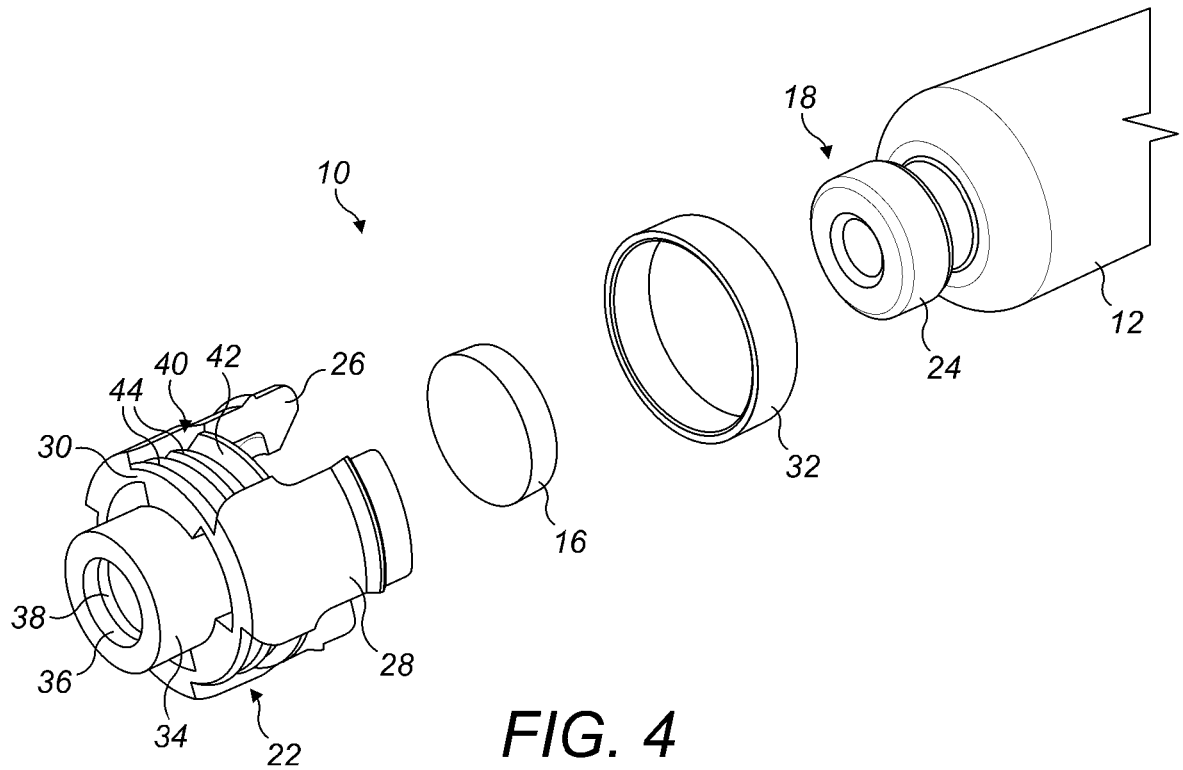
FIG. 4 is an exploded view of part of a medicament container for use in the device of FIG. 1.
Figure 5:
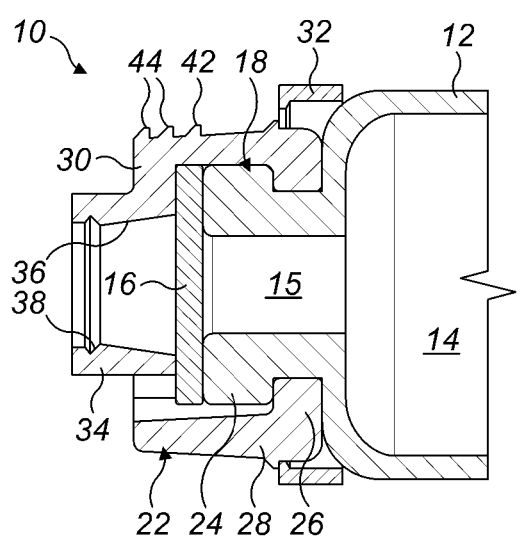
FIG. 5 is a cross-sectional view of part of the medicament container of FIG. 4.

The container 10, which is shown in more detail in FIGS. 4 and 5, comprises a generally tubular body 12 which defines a chamber 14 for containing a medicament substance. A first, forward end of the body 12 defines an outlet 15 of the chamber 14 that is closed by a closure member in the form of an elastomeric disc or septum 16, which seals against the end face of a reduced-diameter neck 18 of the body 12. A piston member or stopper 20 (see FIG. 3, not shown in FIGS. 4 and 5) is received in the opposite, rearward end of the body 12 to close the second end of the chamber 14, so that the medicament substance is contained between the septum 16 and the stopper 20.

As seen most clearly in FIG. 5, the septum 16 is held in place by a coupling element 22 that is in clipped engagement with a collar 24 on the neck 18 of the body 12 by way of clip formations 26. The clip formations 26 are disposed at the ends of a plurality of legs 28 that extend proximally from a ring 30 of the coupling element 22. In the illustrated example, three legs 28 are provided, but fewer or more legs could be present. The legs 28 are held in place by a retaining ring or band 32, which serves to clamp the coupling element 22 to the neck 18 of the body 12.

The ring 30 supports a tubular throat 34 of the coupling element 22. The throat 34 is integrally formed with the coupling element 22, and defines a generally frustoconical bore 36. An inner end of the throat 34 presses against the septum 16 to seal the septum 16 against the end of the neck 18. The circumference of the throat 34 is uninterrupted so that a sealing force is applied to the septum 16 around a complete circle. An annular groove 38 is disposed on the inside of the bore 36 adjacent to the outer end of the throat 34.

The outer wall of the ring 30 of the coupling element 22 is provided with angularly-spaced recesses 40 disposed between each adjacent pair of legs 28. The inner face of each recess 40 is shaped to define a ramp formation 42 at the end of the recess 40 closest to the container body 12, and a pair of axially-spaced ridge formations 44, a first of which is disposed at the end of the recess 40 opposite the ramp formation 42, and the second of which is disposed between the first ridge formation and the ramp formation 42.

Referring back to FIGS. 3(a) and 3(b), the container 10 is arranged in the elongate housing portion 108 with the long axis of the container 10 disposed along the drive axis A and parallel to the contact face 112. The container body 10 is received in a tubular carrier sleeve 114. The forward end of the carrier sleeve 114, closest to the neck 18 of the container 10, comprises an outwardly-directed flange 116. A pair of tabs 118 project from the top and bottom of the flange 116 to engage with slots 120 in the upper and lower housing parts 104, 106 (see FIG. 3(b)) to prevent rotation of the carrier sleeve 114. As shown most clearly in FIG. 2, the opposite, rearward end of the carrier sleeve 114 is formed as a plurality of legs 122 that extend along the container body 12 and terminate with inwardly-directed clip formations 124 that engage with the rearward end of the container 10.

A carrier spring 126, comprising a compression spring, is disposed concentrically around the carrier sleeve 114. The carrier spring 126 bears against the flange 116 of the carrier sleeve 114 at its forward end and against a shoulder 128 formed in the housing 102 at its opposite, rearward end. In this way, the carrier spring 126 biases the carrier sleeve 114, and therefore the container 10, forward towards the needle assembly 130. As will be explained in more detail below, when the device 100 is in the initial state, forward movement of the container 10 towards the needle assembly 130 is blocked by the trigger assembly 250.

Figure 6A:
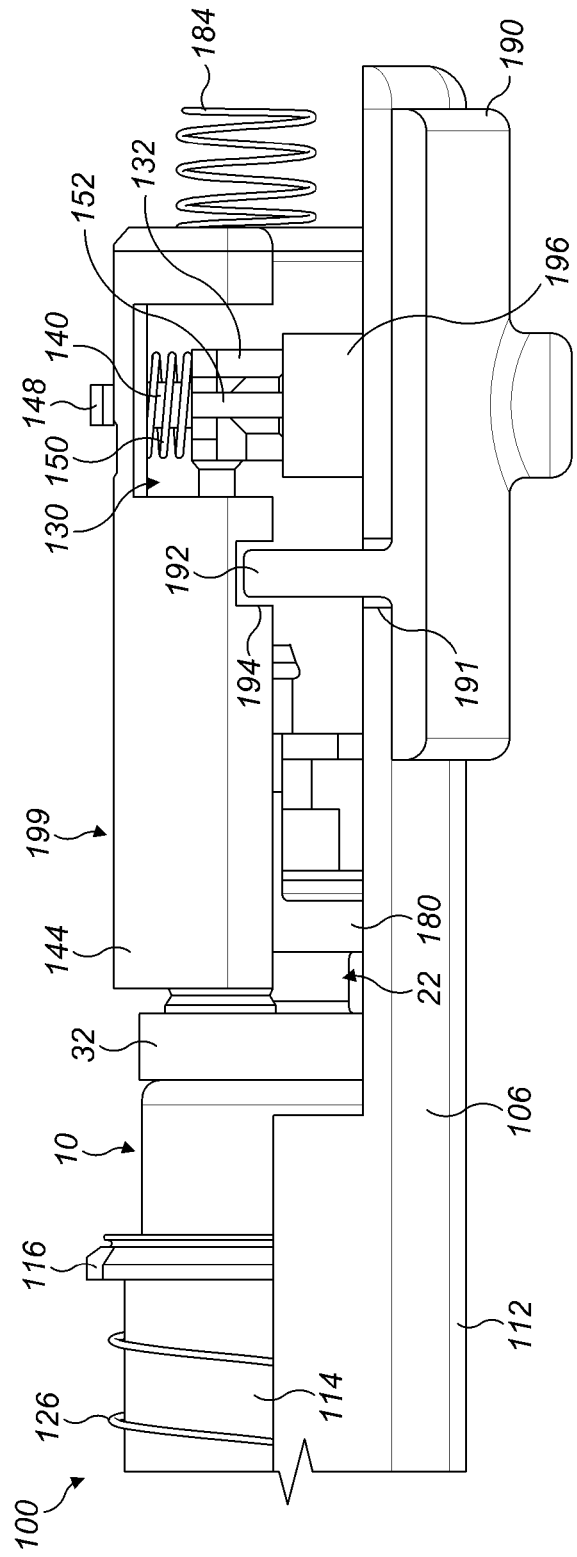
FIG. 6(a) is a side view of part of the delivery device of FIG. 1 in the initial state, with the upper housing part omitted for clarity.
Figure 6B:
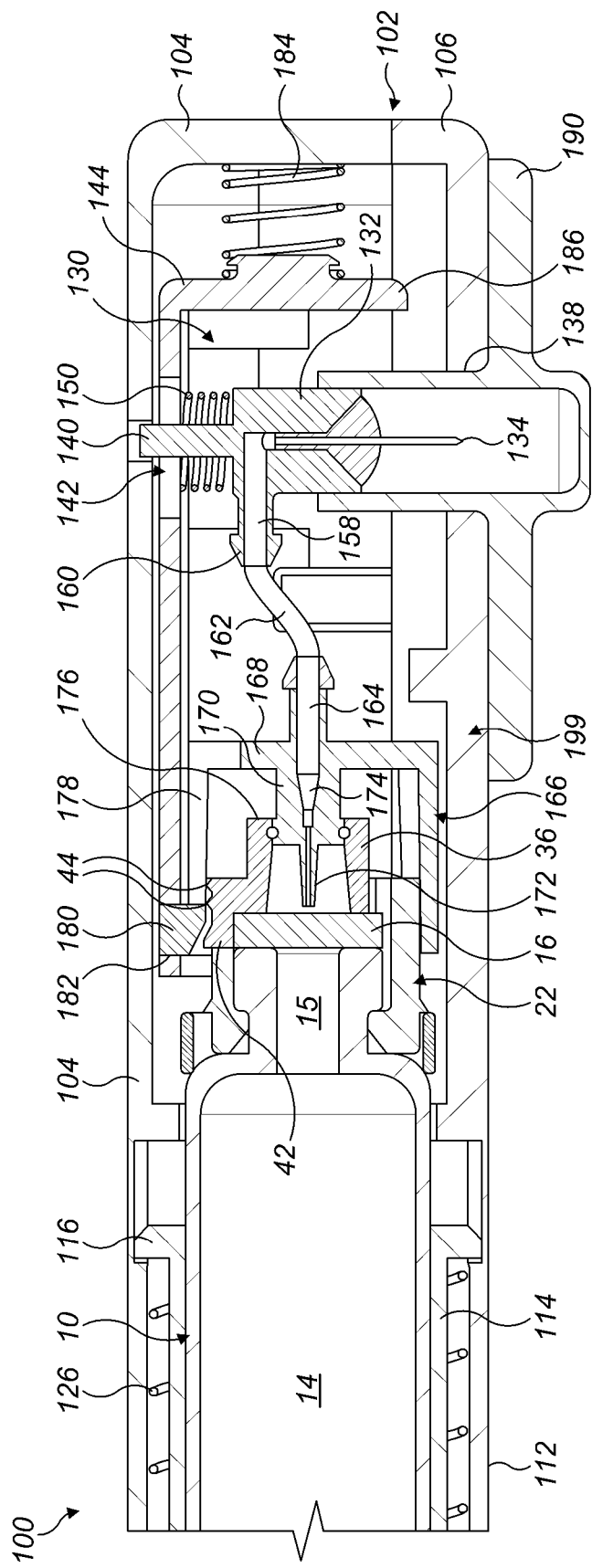
FIG. 6(b) is a corresponding cross-sectional view on a vertical plane with the upper housing part in place.

Referring additionally to FIG. 6, the needle assembly 130 is disposed at the forward end region of the elongate housing portion 108. As shown most clearly in FIG. 6(b), the needle assembly 130 comprises a needle holder 132 having a generally cylindrical body that retains a hypodermic injection needle 134. The injection needle 134 is disposed along an axis that is perpendicular to the drive axis A (and the axis of the container 10), so that the injection needle 134 points towards the contact face 112 of the device 100. The injection needle 134 is aligned with an aperture 136 in the lower housing part 106, and is retained in the needle holder 132 by a suitable sealing material 138.

Figure 2A:
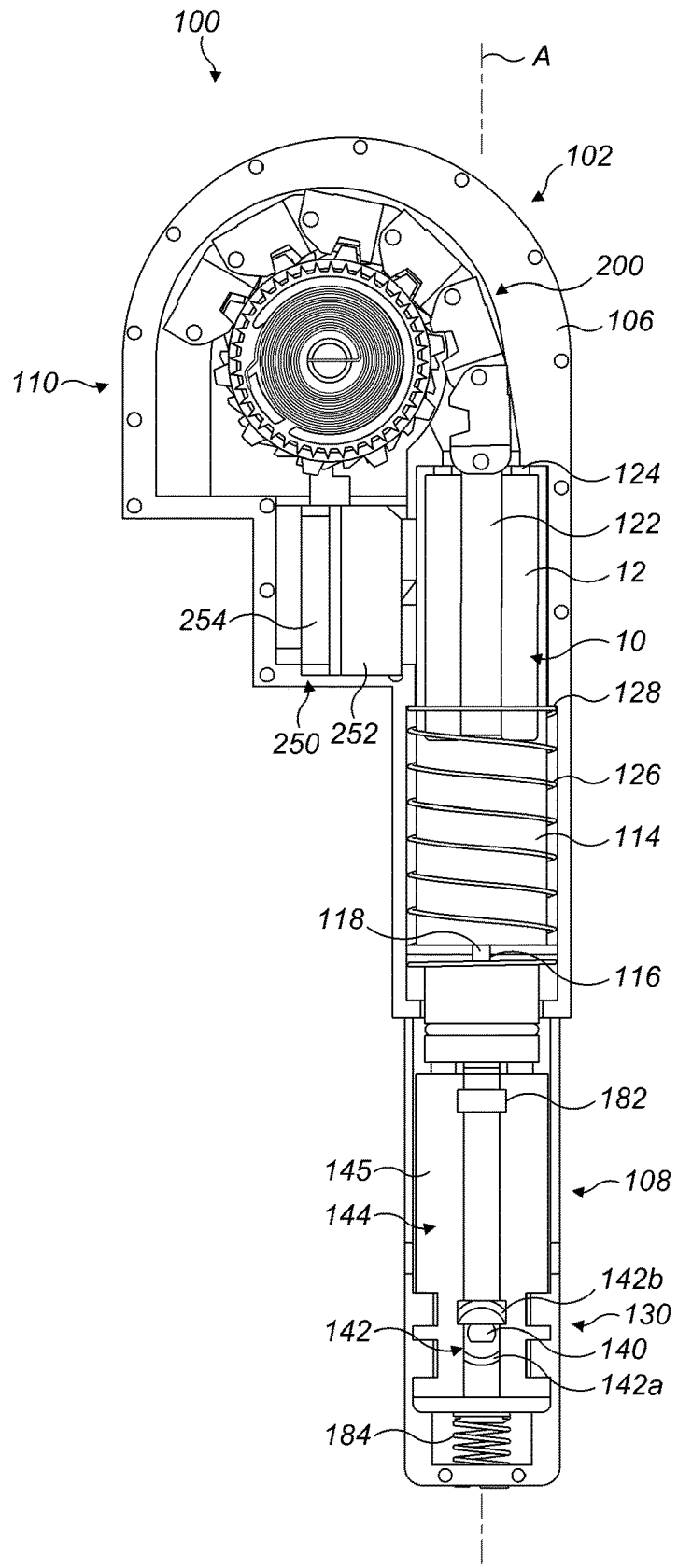
Figure 2B:
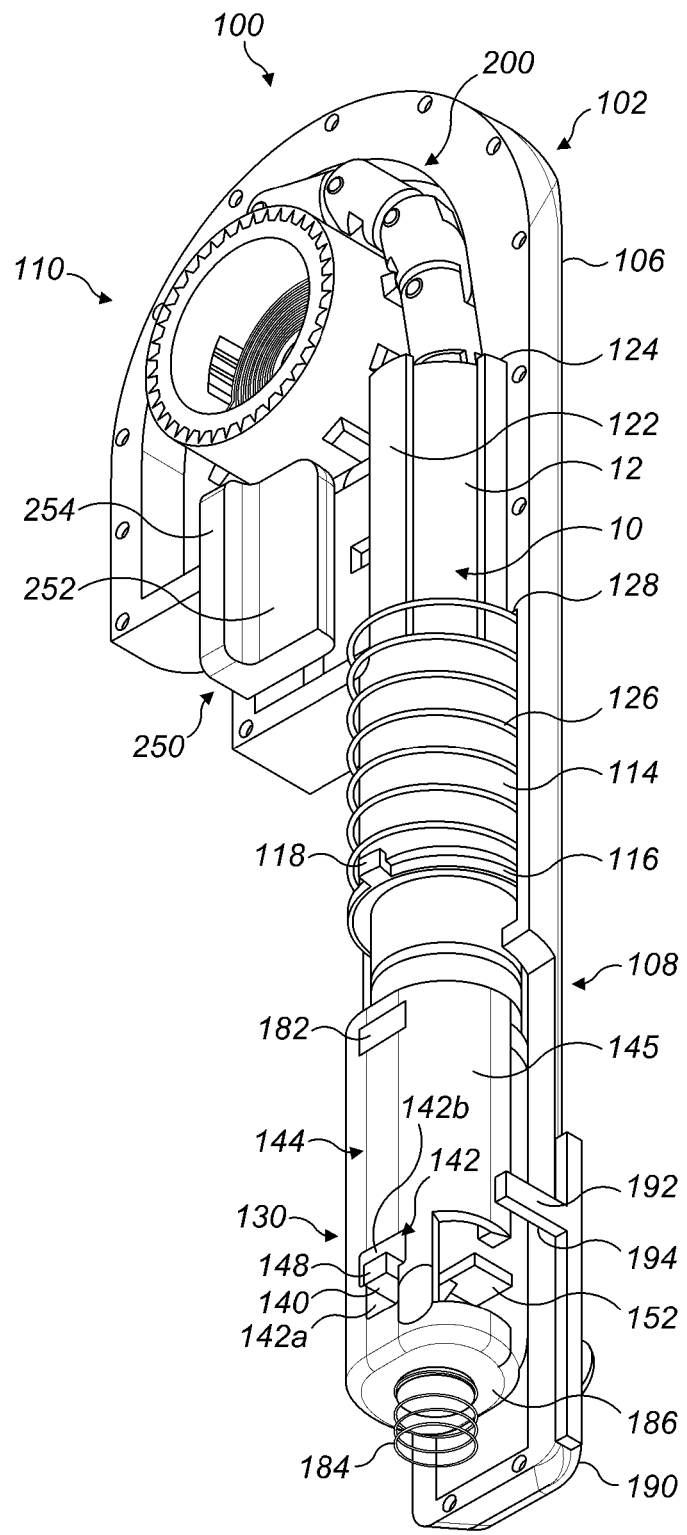

The needle holder 132 is arranged for movement with respect to the housing 102 in an insertion direction parallel to the axis of the needle 134. In the initial state of the device 100, the needle holder 132 is latched in a retracted position, in which the injection needle 134 is concealed within the housing 102. To this end, the needle holder 134 includes a latching member 140 that extends towards the top of the device 100. The latching member 140 extends through a T-shaped slot 142 in a control piece 144 disposed on the top side of the needle assembly 130. Referring to FIG. 2(a), the slot 142 is oriented so that a relatively narrow, elongate part 142a of the slot (corresponding to the stem of the T-shape) extends parallel to the container axis, and so that a wide part 142b of the slot 142 (corresponding to the crossbar of the T-shape) extends laterally with respect to the container axis. The latching member 140 includes an enlarged head 148, seen most clearly in FIG. 2(b), that is wider than the elongate part 142a of the slot 142 such that, when in the initial state, the head 148 of the latching member 140 engages with the top side of the control piece 144 to prevent movement of the needle holder 132 in the downward direction.

A needle insertion spring 150, seen most clearly in FIG. 6, is arranged coaxially around the latching member 140 to bias the needle holder 132 in the insertion direction. A top end of the insertion spring 150 bears against the bottom side of the control piece 144 and a bottom end of the insertion spring 150 bears against the body of the needle holder 132. The needle holder 132 includes a pair of laterally-extending fins 152 (see FIGS. 2(b) and 3(a)) that are guided in guide formations comprising tracks 154 formed in the housing 102 (see FIG. 3(a)) to provide a guide means for guiding the needle holder 132 in the insertion direction, and the projecting head 148 of the latching member 140 is accommodated in a slot 156 formed in the upper housing part 104 opposite the aperture 136 in the lower housing part 106.

Referring again to FIG. 6(b), the needle holder 132 includes an internal passage 158 to fluidly connect the injection needle 134 with a rearwardly-projecting nipple 160 formed on the holder 132. A flexible tube 162 connects the nipple 160 on the needle holder 132 to a corresponding forwardly-projecting nipple 164 formed on a hub 166.

The hub 166 and the control piece 144 form part of a connection arrangement 199 of the device 100 that is operable to establish a fluid connection between the chamber 14 of the container 10 and the injection needle 134. The hub 166 comprises a disc-shaped holder 168 having a tubular, central extension 170 for cooperation with the container coupling element 22. An internal piercing member or internal needle 172 projects rearwardly from the extension 170 towards the container 10, and an internal passage 174 of the hub fluidly connects the piercing member 172 with the nipple 164.

An O-ring 176 is retained by an annular groove on the outer face of the extension 170. When the device 100 is in the initial state, the connection arrangement 199 is in an unconnected configuration in which the hub 166 and the container 10 are arranged in a first attachment position relative to one another. In this first attachment position, the O-ring 176 locates in the annular groove 38 of the throat 36 of the container coupling element 22 and the piercing member 172 does not pierce the septum 16 so that the outlet 15 of the container 10 remains closed. By virtue of the seal formed between the coupling element 22 and the extension 170 by the O-ring 176, the piercing member 172 is kept sterile in an enclosed chamber on the forward side of the septum 16.

The hub 166 comprises a plurality of rearwardly-extending arms 178 that carry clip formations 180 (only one of which is visible in FIG. 6(b)). The clip formations 180 are arranged for engagement with the ramp and rib formations 42, 44 of the coupling element 22. In the first attachment position, each clip formation 180 is located on the forward side of the ramp formation 42 of a respective recess 40 of the coupling element 22, behind the ribs 44.

An upper one of the clips 180 is enlarged to locate in an aperture 182 provided in a part-tubular portion 145 of the control piece 144, as seen most clearly in FIG. 2. In this way, the hub 166 is coupled to the control piece 144 for joint movement along the drive axis A. The control piece 144 and the hub 166 are biased rearwardly by a biasing means comprising a control spring 184. The control spring 184, which forms part of the connection arrangement 199, is a compression spring that is disposed between a vertical end plate 186 of the control piece 144 and the forward end of the elongate housing portion 108.

As seen most clearly in FIG. 6(a), when in the initial state, rearward movement of the control piece 144 and the hub 166 is prevented by a removable shield 190 of the device 100. The shield 190 fits to the lower side of the device 100, to cover the aperture 138 in the contact face 112. A pin 192 extends upwards from the shield 190, through a slot 191 in the lower housing part 106, to cooperate with a cut-out 194 in the control piece 144. Engagement between the pin 192 and the cut-out 194 blocks rearward movement of the control piece 144 when the shield 190 is in place. The shield 190 includes an upstanding, tubular wall that provides a sealing cup 196 for the needle holder 132. As shown in FIG. 6(b), the cup 196 fits around the needle holder 132 to maintain sterility of the injection needle 134 until the shield 190 is removed.

Figure 7A:
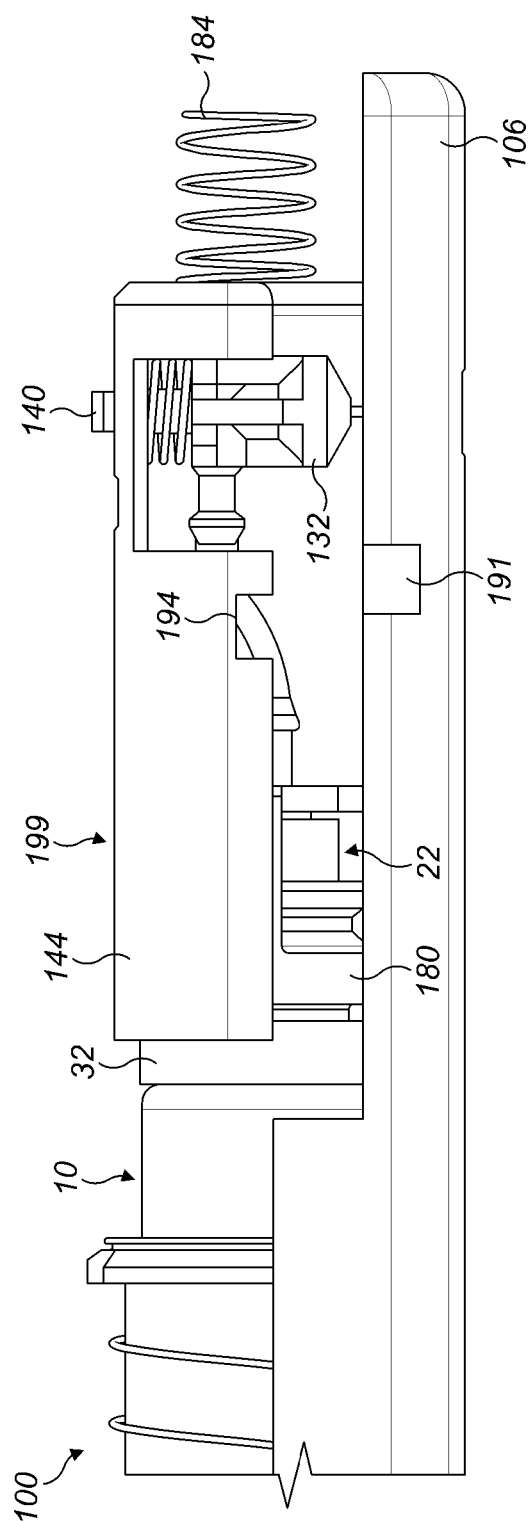
FIG. 7(a) is a side view of part of the delivery device of FIG. 1 after removal of a shield component and with the upper housing part omitted for clarity.

To prepare the device 100 for use, the shield 190 can be removed. Removal of the shield 190 switches the connection arrangement 199 of the device from the initial, unconnected configuration, shown in FIGS. 6(a) and (b), to a connected configuration, which is shown in FIGS. 7(a) and (b). As the shield 190 is withdrawn from the housing 102, the pin 190 moves out of engagement with the control piece 144. The control piece 144 is therefore released for rearward movement towards the container 10 under the force applied by the control spring 184.

Figure 7B:
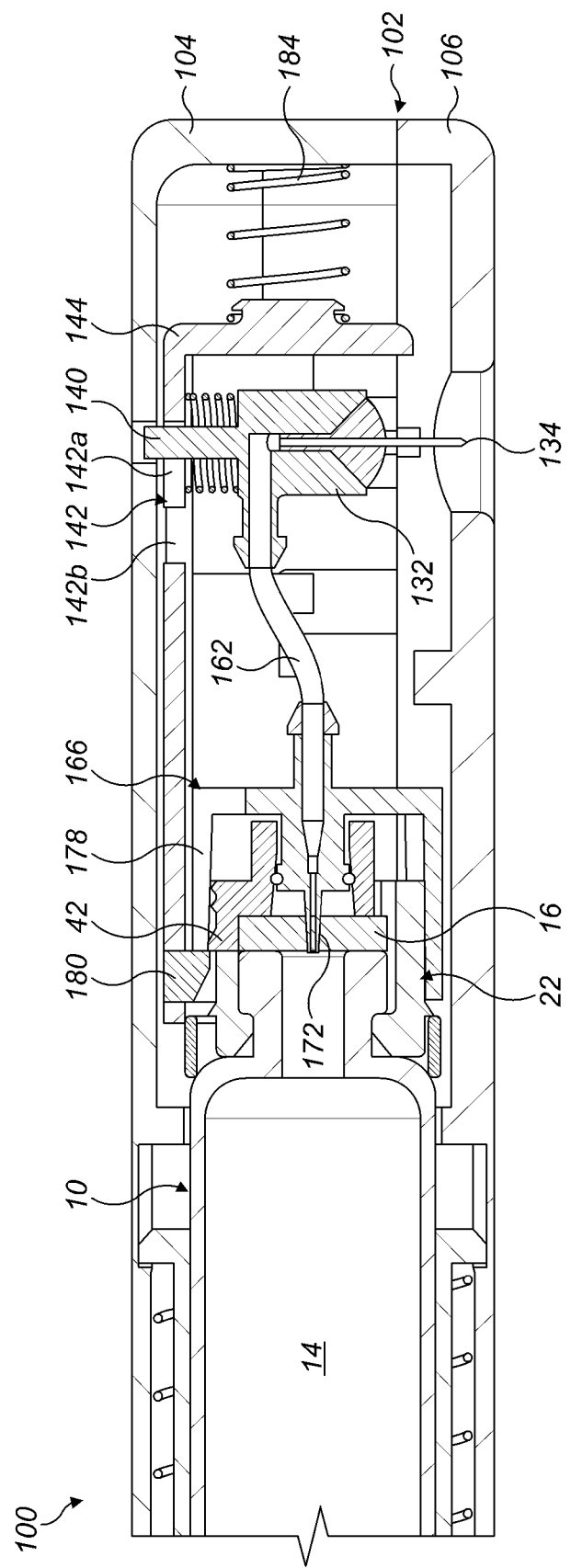
FIG. 7(b) is a corresponding cross-sectional view on a vertical plane with the upper housing part in place.

Rearward movement of the control piece 144 drives rearward movement of the hub 166, causing the hub 166 to move into a second attachment position with respect to the container 10. Referring to FIG. 7(b), as the hub 166 moves towards the container 10, the piercing member 172 pierces the septum 16 to open the outlet 15 so that a connection for fluid flow is established between the medicament chamber 14 and the injection needle 134, through the hub 166, the flexible tube 162 and the needle holder 132.

To secure the hub 166 in position with respect to the container 10, the clips 180 on the arms 178 of the hub 166 move past the ramp formations 42 to engage with the rear side of the corresponding recesses 40 on the coupling element 22 of the container 10.

Upon displacement of the coupling piece 144 towards the container 10, the T-shaped slot 142 moves rearwardly with respect to the latch member 140 of the needle holder 132. To accommodate the latch member 140 at this stage, the elongate part 142a of the T-shaped slot 142 is extended in the forward direction.

When the connection arrangement 199 has been switched to the connected configuration, the device 100 can be positioned for injection. The contact face 112 can be placed against the injection site, with the aperture 136 in the lower housing part 106 positioned at the site where injection is required. The device 100 can be held in position by hand, or by using a strap, patch or other apparatus, or by means of an adhesive applied to the contact face 112 of the device 100.

Injection of the medicament is driven by the drive mechanism 200, which will now be described with reference to FIGS. 8 to 10.

Figure 8:
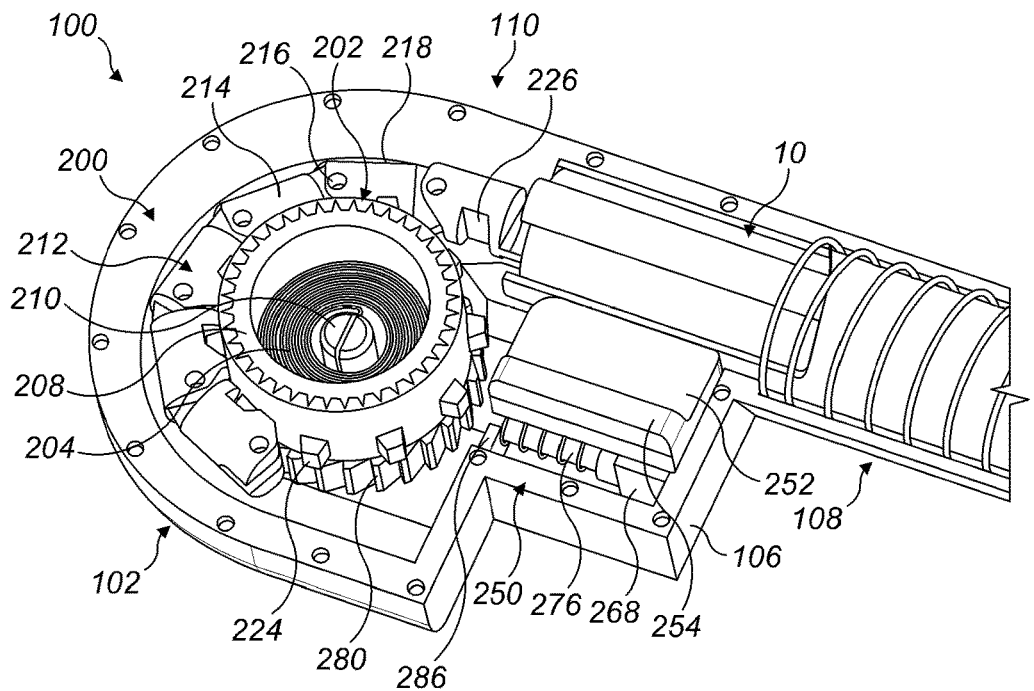
FIG. 8 is an isometric view of part of the delivery device of FIG. 1, with the upper housing part omitted and showing a trigger assembly.
Figure 9:
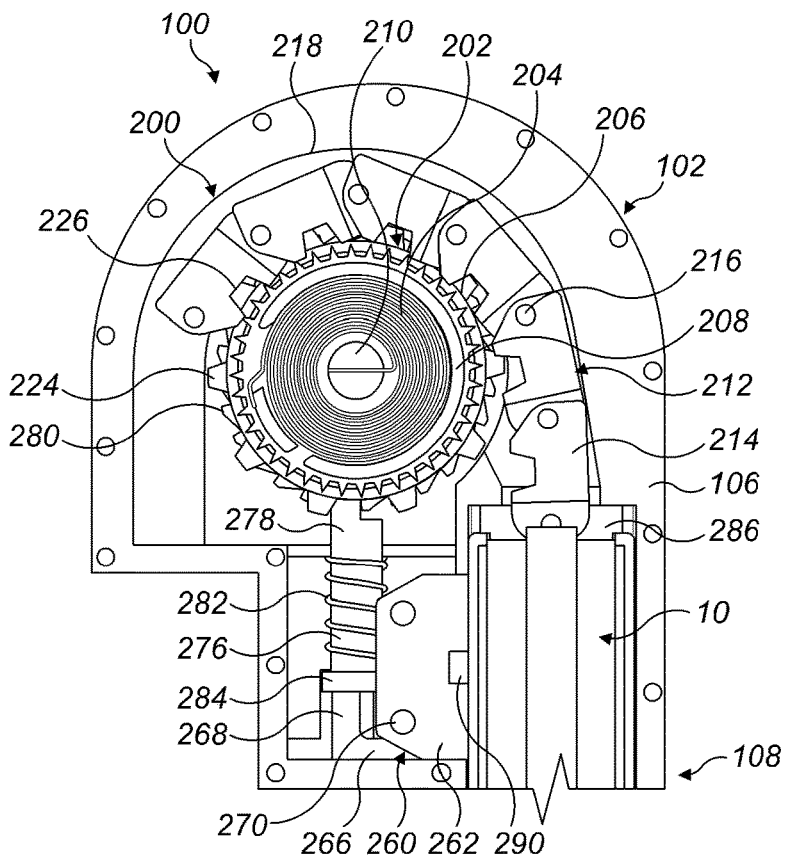
FIG. 9 is a top view of part of the delivery device of FIG. 1, with the upper housing part and part of the trigger assembly omitted.
Figure 10:
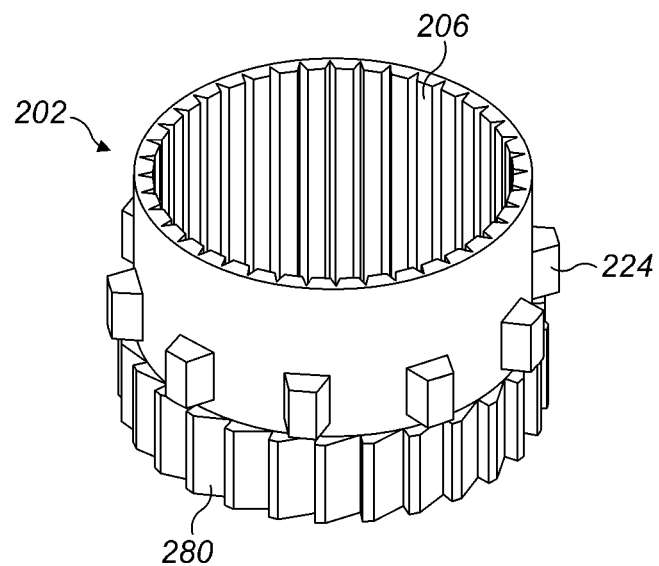
FIG. 10 is an isometric view of a drive member of the device of FIG. 1, in isolation.

Referring first to FIGS. 8 and 9, the drive mechanism 200 is disposed on the rear side of the container 10 in the enlarged portion 110 of the housing 102, and comprises a rotatable drive member 202 that is biased for rotation with respect to the housing 102 by a drive spring 204 in the form of a spiral or power spring. The drive member 202 is generally tubular, and is shown in isolation in FIG. 10. The bore 206 of the drive member 202 is splined to engage with corresponding grooves on a spring coupling part 208, seen in FIGS. 8 and 9, which is mounted concentrically inside the bore 206. An inner end termination of the drive spring 204 is engaged with a boss 210 provided on the lower housing part 106. The outer end termination of the drive spring 204 is attached to the spring coupling part 208, which transfers the torque of the spring 204 to the drive member 202. The drive spring 204 is wound such that, in the initial state of the device 100, the spring 204 biases the drive member 202 in the clockwise direction (in the orientation shown in FIG. 9).

A transmission member, in the form of an interlinked chain 212, is disposed around and engaged with the drive member 202. The chain 212 comprises a plurality of elements 214 that are linked together with pins 216 to allow the chain 212 to bend around the drive member 202, and the housing 102 is formed to provide a guide track 218 for the chain 212. As can be seen most clearly in FIGS. 3(a) and (b), a free end 220 of the chain 212 is aligned with the drive axis A to form a drive element for cooperation with the stopper 20 of the container 10. When in the initial position, the free end 220 of the chain 212 extends into the rear end of the body 12 of the container 10, and a washer 222 is provided to centre the chain 212 in the body 12.

The drive member 202 includes a set of teeth 224 for engagement with corresponding recesses 226 in each of the chain elements 214, so that rotation of the drive element 202 causes movement of the free end 220 of the chain 212 in the forward direction towards the stopper 20. However, before activation of the drive mechanism 200, rotation of the drive member 202 is blocked by the trigger assembly 250, as will be explained in more detail below.

Referring first to FIGS. 1, 2 and 8, the trigger assembly 250 comprises a slider component 252 that is mounted on the top side of the upper housing part 104. The slider component 252, shown in isolation in FIG. 11(a), has an upstanding ridge 254 to allow the slider component 252 to be moved laterally by a user. A pair of pins 256 extend downwardly from a raised step 258 on the bottom side of the slider component 252 to engage with a lock member 260 mounted in the housing 102.

The lock member 260, which is shown in isolation in FIG. 11(b), comprises a top plate 262, a side wall 264 that depends from one side of the top plate 262, and a lock arm 266 that projects laterally from the side wall. A blocking element 268 is provided on the side of the lock arm 266 closest to the drive member 202. A pair of holes 270 are provided in the top plate 262 to receive the pins 256 of the slider component 252.

The upper housing part 104, part of which is shown in isolation in FIG. 12, comprises an aperture 272 in which the step 258 of the slider component 252 is received when the device 100 is assembled. A pair of projections 274 are provided on opposite sides of the aperture 272. When the slider component 252 is in place, the projections 274 cooperate with the step 258 to hold the slider component 252 in an initial position, with the step 258 located on the side of the projections 274 closest to the container. In use, the slider component 252 can be moved laterally, away from the container 10, into a second position in which the step 258 is located on the side of the projections 274 farthest from the container 10. The user must apply sufficient lateral force to the slider component 252 to push the step 258 past the projections 274, which helps to prevent accidental operation of the device 100.

Referring to FIG. 13(a), which is an enlarged cross-sectional view corresponding to FIG. 3(a), the trigger assembly 250 includes a trigger pin 276 that is arranged parallel to the container axis. The end 278 of the trigger pin 276 is shaped to engage with a set of ratchet teeth 280 on the drive member 202. The trigger pin 276 is biased in the forward direction, away from the drive member 202, by a trigger spring 282 that acts between a collar 284 on the trigger pin 276 and an internal wall 286 of the housing 102. The trigger pin 276 is guided along a track (not shown) in the housing 102 and in an aperture of the internal wall 286.

When the slider component 252 is in the initial position, the trigger pin 276 is held in engagement with one of the ratchet teeth 280 of the drive member 202 by the blocking element 268 of the lock arm 266 of the lock member 260. In this condition, the trigger pin 276 acts as a pawl to prevent rotation of the drive member 202 under the torque of the drive spring 204, thereby preventing movement of the chain 212.

The lock member 260 also cooperates with the carrier sleeve 114 to prevent forward movement of the container 10 when the slider component 252 is in the initial position. To this end, the carrier sleeve 114 is provided with a wedge-shaped catch 288 that projects laterally from the leg 122 of the carrier sleeve 114 closest to the trigger assembly 250. The side wall 264 of the lock member 260 includes an aperture 290 for receiving the catch 288 when the slider component 114 is in the initial position, so that a vertical face of the catch 288 abuts the edge of the aperture 290 to block forward movement of the carrier sleeve 114.

Movement of the slider component 252 out of the initial position results in sequential unlocking first of the carrier sleeve 114 as the slider component 252 reaches an intermediate position, and then of the drive mechanism 200 as the slide component 252 moves to a second position. Accordingly, as shown in FIG. 13(*b*), when the slider component 252 is first moved away from the initial position, the side wall 264 of the lock member 260 moves laterally so that the catch 288 of the carrier sleeve 114 emerges from the aperture 290. The container 10 is now free to move forward, under the influence of the carrier spring 126 (not visible in FIG. 13).

Forward movement of the container 10 triggers deployment of the needle 134 to pierce the injection site, as will now be explained. FIGS. 14(*a*) and 15(*a*) show the forward end of the device before insertion of the needle 134, and FIGS. 14(*b*) and 15(*b*) are corresponding views after needle deployment.

Upon movement of the slider component 252 out of the initial position, the control piece 144 moves forward with the container 10, bringing the laterally-extending part 142*b* of the T-shaped slot 142 into alignment with the head 148 of the latch member 140 of the needle holder 132, as best seen in FIG. 14(*b*). This releases the latch member 140 from engagement with the control piece 144, so that the needle holder 132 moves downwards in the insertion direction under the influence of the insertion spring 150. In this way, the needle 134 is extended through the aperture 138 in the lower housing part 106 and into the injection site. The tube 162 flexes to maintain fluid communication between the container 10 and the needle 134.

Referring back to FIG. 13(*b*), the blocking element 268 of the lock member 266 is arranged so that, when the catch 288 on the carrier sleeve 114 is released from the aperture 290, the blocking element 268 remains in abutment with the trigger pin 276. In this way, needle insertion occurs before the drive mechanism 200 is released.

Further movement of the slider component 252 in the lateral direction causes the blocking element 268 of the lock member 260 to move clear of the end of the trigger pin 276. The trigger pin 276 is then able to move out of engagement with the drive member 202, under the influence of the trigger spring 282, as shown in FIG. 13(*c*).

The drive member 202 is now free to rotate in the clockwise direction under the influence of the drive spring 204. Rotation of the drive member 202 causes the free end 220 of the chain 212 to move forwards towards the stopper 20. Initially, the free end 220 of the chain 212 moves forward to close the gap between the initial position of the free end 212 and the stopper 20, and then the chain 212 contacts and drives forward the stopper 20 to expel medicament through the needle 134. FIG. 16 shows the device 100 at the end of medicament delivery, when the stopper 20 has been pushed to the forward end of the chamber 14.

After medicament delivery is complete, the device 100 can be removed from the injection site and disposed of.

To summarise, in an operating sequence of the device of the first embodiment of the invention, the shield 190 is first removed by the user. Removal of the shield exposes the needle 134 and switches the connection arrangement 199 into the connected configuration. The device can then be positioned against the injection site, and the slider component 252 can be moved by the user from its starting position to the second position. Operation of the slider component 252 first causes insertion of the needle 134 as the slider component 252 passes through the intermediate position, and then activation of the drive mechanism 200 for delivery of the medicament as the slider component 252 reaches the second position. In this way, only two user operations are required to initiate all of the steps in the operating sequence.

Figure 17B:
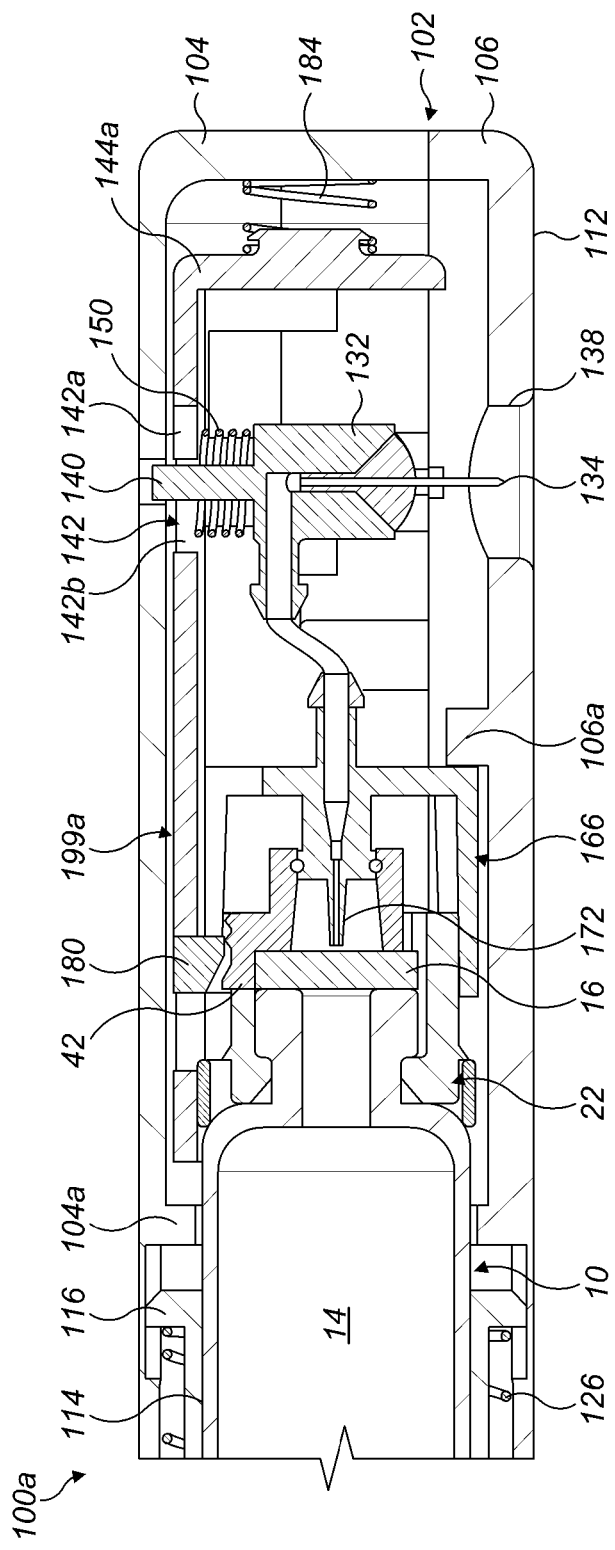

FIG. 17 illustrates a device 100*a* according to a variant of the first embodiment of the invention. The device 100*a* shares many parts with the device 100 of FIGS. 1 to 16, and so only the differences will be described and like reference numerals are used for like parts.

In the variant of FIG. 17, relative movement between the hub 166 and the cartridge 10 to switch the connection arrangement 199*a* from the unconnected state to the connected state is driven by the container spring 126, instead of by the control spring 184. Thus, in this variant, the container spring 126 forms part of the connection arrangement 199*a*, and switching of the connection arrangement 199*a* occurs in response to operation of the trigger assembly 250 (not shown in FIG. 17), rather than upon removal of the shield 190.

Referring to FIG. 17(*a*), which is a cross-sectional view of the device 100*a* in an initial state and corresponds to the view shown in FIG. 6(*b*), in this variant the control piece 144*a* is extended rearwardly to abut against a stop 104*a* formed on the upper housing part 104. Upon removal of the shield 190, cooperation between the control piece 144*a* and the stop 104*a* prevents the control piece 144*a* from moving rearwardly with respect to the housing 102, and hence with respect to the cartridge 10. Accordingly, the connection arrangement 199*a* remains in the unconnected state and does not switch to the connected state upon removal of the shield 190.

After removal of the shield 190, the device 100*a* can be placed against the injection site and, as described above with reference to FIGS. 13 to 15, the slider component 252 of the trigger assembly 250 (not shown in FIG. 17) can be moved laterally with respect to the housing 102 to initiate the firing sequence of the device 100*a*. Thus, initial movement of the slider component 252 causes forward movement of the container 10 under the influence of the container spring 126 when the lock member 290 disengages from the catch 288 of the carrier sleeve 114 (see FIG. 13).

Initially, the hub 166 moves forward with the container 10, as a result of the frictional engagement between the clips 180 and the hub 166. In particular, the clips 180 remain on the forward side of the ramp formations 42 of the hub 166. The upper clip 180 drives the control piece 144*a* forward to bring the laterally-extending part 142*b* of the T-shaped slot 142 into alignment with the head of the latch member 140 of the needle holder 132, as shown in FIG. 17(*b*). This releases the latch member 140 from engagement with the control piece 144*a*, so that the needle holder 132 moves downwards in the insertion direction under the influence of the insertion spring 150. At this time, the connection arrangement 199*a* is still in the unconnected state.

Figure 17C:
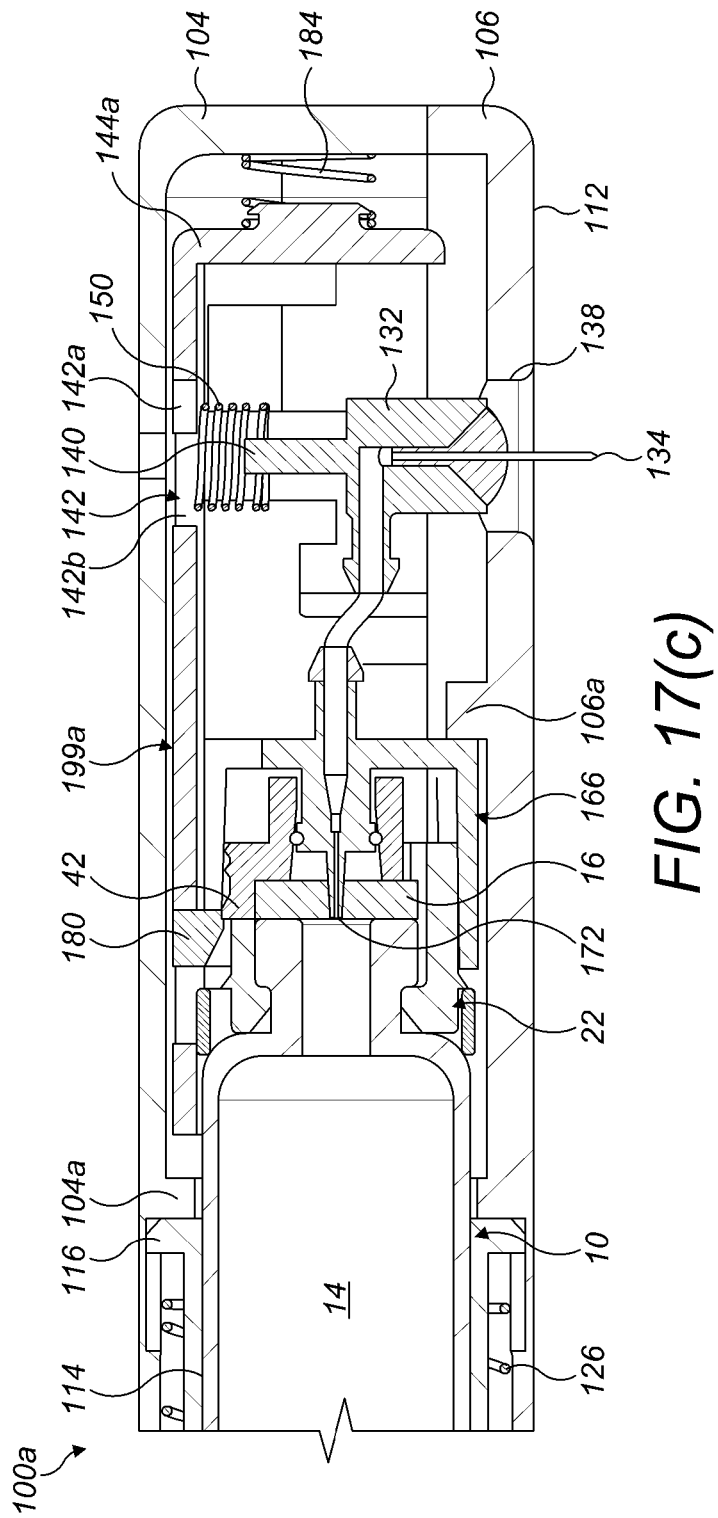

After insertion of the needle 134, forward movement of the container 10 continues under the influence of the container spring 126. However, further forward movement of the hub 166 is prevented by abutment between the hub 166 and a stop 106*a* formed in the lower housing body 106. Now, the ramp formations 42 of the coupling element 22 pass under the clips 180 of the hub 166, and, the coupling element 22 of the container 10 moves forwards with respect to the hub 166 to switch the connection arrangement 199a into the connected state, as shown in FIG. 17(c). As described above, when in the connected state, the clips 180 of the hub 166 engage with the rear side of the ramp formations 42 and the piercing member 172 pierces the septum 16 to establish a fluid connection between the chamber 14 of the cartridge 10 and the needle 134.

Further operation of the device 100a of FIG. 17 is as described with reference to FIGS. 1 to 16.

In the variant of FIG. 17, the strength of the control spring 184 and the frictional resistance that must be overcome for the clips 180 of the hub 166 to pass over the ramp formations 42 of the coupling element 22 are such that needle insertion occurs before switching of the connection arrangement 199a to the connected state. If preferred, however, the device 100a can be arranged so that switching of the connection arrangement 199a to the connected state occurs before needle insertion, for example by the provision of a stronger control spring 184 and/or a lower frictional resistance between the clips 180 and the coupling element 22.

FIGS. 18 to 32 illustrate a device 300 according to a second embodiment of the invention. The device 300 of the second embodiment is suitable for use with a medicament of the type that requires mixing of two medicament substances before delivery.

Referring first to FIGS. 18 and 19, the device 300 comprises a generally elongate housing 302 having an upper housing part 304 and a lower housing part 306. A bottom surface of the lower housing part 306 provides a contact face 312 of the device. In an initial state of the device, a shield 390 is removably attached to the bottom of the device 300 to cover a majority of the contact face 312. A trigger button 450 extends across the top of the housing 302 and forms part of a trigger assembly of the device 300.

As shown in FIG. 19, a medicament cartridge 50 is received in the housing 302, with the long axis of the cartridge 50 disposed along a drive axis A of the device 300. The medicament cartridge 50 comprises a first or outer container 10 that is substantially identical to the container 10 described above with reference to FIGS. 3 to 5. However, in place of the stopper, the cartridge 50 includes a second, inner container 51 that is telescopably received in the rearward end of the outer container 10.

The chamber of the outer container 10 thus defines a first chamber 14 for containing a first medicament substance, which is typically a solid substance (for example in powdered, lyophilised) form. The first chamber 14 is closed by the inner container 51. The inner container 51 comprises a generally tubular body 52 which defines a second chamber 54 for containing a second medicament substance, typically a liquid for reconstitution of the first substance. The inner container body 52 is similar in shape and construction to the first container body 12, and thus comprises a neck 58 and a collar 64 that extends around the neck 58 at its forward end.

An elastomeric bung or stopper 70 is received in the outer container body 52 to close the rearward end of the second chamber 54. The forward end of the inner container body 52 is closed by a second or inner closure member in the form of a cap 80 that fits over the collar 64.

The cap 80 is formed from an elastomeric material, such as a halobutyl or other rubber material, and comprises a forward face 82 and an annular ring part 84 that extends rearwardly from the forward face 82 to receive the neck 58 of the inner container body 52. The ring part 84 is shaped to engage around and form a seal against the neck 58 on the rearward side of the collar 64 to secure the cap 80 to the inner container body 52. The cap 80 has an outer diameter that is sized so that a seal is formed between the cap 80 and the inner wall of the outer container body 12.

The distal face 82 of the cap 80 is formed to provide a one-way slit valve 86 for closing the forward end of the second chamber 54. To this end, the distal face 82 comprises a generally wedge-shaped region 88 that faces away from the second chamber 54 (i.e. the ridge of the wedge-shaped region 88 extends from the forward side of the cap 80), and a slit extends through the cap 80 along the ridge to divide the wedge-shaped region 88 into a pair of valve members 90. The valve members 90 are biased towards one another so that, when fluid pressures on each side of the slit valve 86 are equal, the valve members 90 seal against one another to close the slit. When the pressure on the rearward side of the slit valve 86 is sufficiently greater than the pressure on the forward side, the bias of the valve members 90 can be overcome to allow fluid flow through the slit valve 86 in the forward direction. However, when the pressure on the forward side of the slit valve 86 exceeds the pressure on the rearward side, the valve 86 closes.

Referring additionally to FIG. 20, a needle assembly 330 and a connection arrangement 399 are disposed at the forward end of the housing 102. The needle assembly 330 is generally similar to the needle assembly 130 of the first embodiment of the invention, and thus comprises a needle holder 332 having a generally cylindrical body that retains a hypodermic injection needle 334 in a vertical orientation.

The needle holder 332, which is shown in isolation in FIG. 21, includes a pair of latching arms 340 that extend upwardly towards the top of the device 300. The top end of each latching arm 340 is provided with an outwardly-facing clip formation 348. In the initial state of the device 300, the latching arms 340 extend through a slot 342 in a control piece 344 of the connection arrangement 399, which is shown in isolation in FIG. 22. As most clearly seen in FIG. 20, the clip formations 348 engage with the top rim of the slot 342 to latch the needle holder 332 to the control piece 344.

Referring again to FIGS. 19 and 20, a needle insertion spring 350 is arranged around the latching arms 340, with a top end of the insertion spring 350 bearing against the bottom side of the control piece 344 and a bottom end of the insertion spring 350 bearing against the body of the needle holder 332.

The needle holder 332 includes a pair of laterally-extending fins 352 (not visible in FIG. 19) that are guided in a track 354 formed between respective pairs of upstanding ribs formed in a carriage piece 355 to provide a guide means for guiding movement of the needle holder 332 vertically with respect to the housing 302, in an insertion direction. The carriage piece 355, which is shown in isolation in FIGS. 23(a) and (b), is part-tubular and is slidable with respect to the housing 302, as will be explained in more detail below. The carriage piece 355 is arranged beneath the needle assembly 330 and includes an aperture 356 that is aligned with the injection needle 334, and a triangular clip 357 is disposed on the lower surface of the carriage piece 355 on the forward side of the aperture 356.

Referring again to FIGS. 19 and 20, the connection arrangement 399 includes a hub 166 that is substantially identical to the hub of the first embodiment of the invention. In this case, an upper one of the clips 180 of the hub locates in a notch 382 provided at the rearward end of the control piece 344 (see FIG. 22) to couple the hub 166 to the control piece 344. The control piece 344 and the hub 166 are biased rearwardly by a control spring 384. As in the first embodiment of the invention, in this second embodiment the control spring 384 is a compression spring that is disposed between a vertical end plate 386 of the control piece 344 and the forward end of the housing portion 102. The vertical end plate 386 is provided with a cylindrical boss 387 to retain the control spring 384.

In the initial state of the device 300, the connection arrangement 399 is in an unconnected configuration, in which the hub 166 is coupled to the cartridge 50 in a first attachment position. In the first attachment position, the O-ring 176 of the hub 166 locates in the annular groove 38 of the throat 36 of the coupling element 22 of the outer container 10 of the cartridge 50, and in which the piercing member 172 of the hub 166 does not pierce the septum 16 of the cartridge 50. A U-shaped locking collar 389, which is shown in isolation in FIG. 24, is disposed between the retaining ring 32 of the cartridge 50 and the hub 166 to prevent relative movement between the hub 166 and the cartridge 50.

FIG. 25 shows the trigger button 450 in isolation. As will be explained further below, the trigger button 450 includes a pair of downwardly-projecting legs 451 that are arranged to move the locking collar 389 upon operation of the trigger button 450 to allow relative movement between the cartridge 50 and the hub 166.

Referring back to FIGS. 19 and 20, the needle holder 332 includes an internal passage 358 to fluidly connect the injection needle 334 with a rearwardly-projecting nipple 360 formed on the holder 332. A flexible tube 362 connects the nipple 360 on the needle holder 332 to the forwardly-projecting nipple 164 of the hub 166.

As shown in FIG. 19, the device 300 includes a drive mechanism 400 that is disposed at the rearward end of the device 300. In this case, the drive mechanism 400 has a linear arrangement with respect to the cartridge 50, and comprises a primary drive element or mixing element 402 for performing a mixing stroke of the device and a secondary or delivery drive element 410 for performing a delivery stroke of the device, as will be explained in more detail below.

The mixing element is in the form of a plunger 402 having a head part 404 at its forward end and an elongate shaft part 406 that extends rearwardly from the head part 404. The plunger 402 is partially received in the rearward end of the inner container body 52 so that the head part 404 of the plunger 402 can cooperate with the stopper 70 of the inner container 50. A mixing spring 408, comprising a compression spring, is arranged concentrically around the shaft part 406 of the plunger 402, so that the forward end of the mixing spring 408 bears against the head part 404.

The rearward end of the mixing spring 408 bears against the delivery drive element 410, which is clamped to the rearward end of the inner container body 52. To this end, the delivery drive element 410 comprises a clamping collar 412, a latching cap 414, and a clamping ring 416 comprising an elastomeric O-ring. The collar 412 is disposed annularly around the inner container body 52, adjacent to its rearward end, and is externally threaded to mate with an internally threaded rim of the latching cap 414.

The clamping ring 416 is sized to conform to the outer diameter of the inner container body 52. During assembly of the device 300, the clamping collar 412 can be turned with respect to the latching cap 414 to squeeze the clamping ring 416 against the outer wall of the inner container body 52. The radial clamping force thus applied by the clamping ring 416 to the inner container body 52 locks the inner container body 52 to the delivery drive element 410.

The collar 412 comprises an outwardly-directed flange 418 that acts as a seat for the forward end of a delivery drive spring 420, comprising a compression spring. The delivery drive spring 420 is arranged concentrically around the latching cap 414, and a rearward end of the delivery drive spring 420 bears against a rearward end wall 422 of the housing 302.

When the device 300 is in the initial state, both the plunger 402 and the delivery drive element 410 are latched in respective starting positions, as will now be explained with reference to FIG. 26, which is a cut-away view of the rearward end of the device 300 with the upper housing part 304 omitted for clarity, and FIG. 27, which shows the latching cap 414 in isolation.

Referring first to FIG. 26, when in the starting position, the shaft part 406 of the plunger 402 extends rearwardly through an opening 424 in the latching cap 414. The shaft part 406 is provided with side ribs 426 and the opening 424 is suitably shaped so that the side ribs 426 prevent rotation of the plunger 402 with respect to the latching cap 414. The shaft part 406 of the plunger 402 includes a slot 428 that receives a pin 392 that extends upwardly from the shield 390, through an opening 430 in the lower housing part 306. Thus, when the shield 390 is in place, the pin 392 prevents movement of the plunger 402 and the mixing spring 408 (not visible in FIG. 26) remains compressed.

Referring additionally to FIG. 27, the latching cap 414 of the delivery drive element 410 includes a pair of rearwardly-extending arms 432. An outwardly-facing clip 434 is disposed at the free end of each arm 432. When in the initial state, the clips 434 engage with respective steps (not shown) formed in the upper housing part 304. A pair of latch release pins 452 (see also FIG. 25) extend downwardly from the trigger button 450 towards the arms 432, through slots (not shown) in the upper housing part 304. The release pins 452 do not contact the arms 432 when the device 300 is in the initial state, so that the delivery drive element 410 remains latched to the upper housing part 304 with the delivery drive spring 420 also in a compressed state. Furthermore, if the trigger button 450 were to be depressed before removal of the shield 390, release of the delivery drive spring 420 is constrained because movement of the cartridge 50 with respect to the housing 102 is prevented by the interactions between the coupling element 22, the locking collar 389, the hub 166, the control piece 344, the needle holder 332 and the shield 390.

Referring back to FIGS. 19 and 20, both the shield 390 and the trigger button 450 are arranged to interact additionally with the needle assembly 330.

Thus the shield 390 includes, at its forward end, an upstanding tubular wall that provides a sealing cup 396 for the needle holder 332. The cup 396 extends upwards through the rearward end of an elongate slot 336 in the lower housing body 306, and through the aperture 356 in the carriage piece 355, and fits around the needle holder 332 to maintain sterility of the injection needle 334 until the shield 390 is removed.

The trigger button 450 includes a downwardly-extending tubular release element 454, as can be seen most clearly in FIG. 25. As will be explained in more detail below, the release element 454 extends through an opening 456 in the upper housing part 304 to cooperate with the latching arms 340 of the needle holder 332 upon operation of the trigger button 450 when the device is in a mixed state, as will be described below. However, in the initial state of the device 300 (as shown in FIGS. 19 and 20), the needle holder 332 is disposed rearwardly with respect to the opening 456, so that the release element 454 is not aligned with the latching arms 340. In this way, operation of the trigger button 450 in the initial state of the device 300, with the shield 390 in place, has no effect on the needle holder 332.

A button spring 460 is disposed concentrically around the release element 454 and acts between the trigger button 450 and the upper housing part 304 to bias the trigger button 450 upwards and away from the housing 302. In this way, in the initial state of the device, the release pins 452 and the release element 454 of the trigger button 450 are kept spaced from the arms 432 of the delivery drive member 410 and the latching arms 340 of the needle holder 332, respectively. Although not illustrated, one or more further springs (which may be compression springs similar to the button spring 460, or other suitable springs) may be provided to resist downward movement of the trigger button 450.

To operate the device 300, the user first removes the shield 390 from the bottom of the device 300, exposing the whole of the contact face 312. Removal of the shield 390 switches the device 300 into a mixed state, as shown in FIG. 28.

Upon removal of the shield 390, the sealing cup 396 is withdrawn from the needle holder 332, and the pin 392 is withdrawn from engagement with the plunger 402. Consequently, the plunger 402 moves forwardly with respect to the housing 302 under the force applied by the mixing spring 408.

The outer container 10 of the cartridge 50 is constrained by engagement of the latching cap 414 of the delivery drive element 410 with the housing 302, so that forward movement of the plunger 402 causes displacement of the stopper 70 towards the cap 80 of the inner container 51 in a mixing stroke of the device 300. Movement of the stopper 70 increases the pressure in the second chamber 54, causing the valve 86 in the cap 80 to open. The substance in the second chamber 54 thus flows through the valve 86 and into the first chamber 14 to mix with the first substance.

To accommodate the increased volume in the first chamber 14, the outer container 10 moves forwardly with respect to the inner container 51 and the housing 302, which results in forward movement of the needle assembly 330, the hub 166, the control piece 344 and the carriage piece 355. In particular, the locking collar 389 prevents relative movement between the coupling element 22 of the cartridge 50 and the hub 166, so that the hub 166 moves forwardly with the outer container 10. The control piece 344 is likewise driven forward, due to engagement between the upper clip 180 and the notch 382 in the control piece 344, and resulting in compression of the control spring 384. As a result of the engagement between the latching arms 340 and the control piece 344, the needle holder 332 moves forward with the control piece 344 into alignment with the aperture 456 in the upper housing part 304, and finally the carriage piece 355 is carried forward by engagement of the fins 352 (not shown in FIG. 28) of the needle holder 332 with the track 354 of the carriage piece 355.

As shown most clearly in FIG. 29, which is a view of the underside of the forward end of the device 300, the triangular clip 357 of the carriage piece 355 engages with a catch 337 disposed at the forward end of the elongate slot 336 in the lower housing body 306. Thus, once in the mixed state, the carriage piece 355 is locked in its forward position with respect to the housing 302.

It will be appreciated from FIG. 28 that, during the mixing stroke, the connection arrangement 399 remains held in the unconnected configuration, with the locking collar 389 stopping the hub 166 and the coupling element 22 moving toward one another. Thus the hub 166 remains in the first attachment position with respect to the cartridge 50, so that the piercing member 172 of the hub 166 does not pierce the septum 16 of the cartridge.

At the end of the mixing stroke, with the carriage piece 355 locked in the forward position, further movement of the needle holder 332 along the drive axis A is prevented. In turn, engagement of the latching arms 340 of the needle holder 332 with the slot 342 of the control piece 344 blocks rearward movement of the control piece 344.

When in the mixed state, the device 300 can be placed against an injection site, with the contact face 312 in contact with the patient's skin. To commence an injection, the trigger button 450 is displaced downwardly towards the housing 302. This triggers several actions within the device 300, as will now be explained with reference to FIGS. 30 to 32.

First, referring to FIG. 30(*a*), an initial downward movement of the trigger button 450 from its initial position to an intermediate position causes the release element 454 to engage with the latching arms 340 of the needle holder 332, which is now aligned with the release element 454. The release element 454 causes the latching arms 340 to bend towards one another to release the clip formations 348 from the rim of the slot 342, which allows the needle holder 332 to disengage from the control piece 344 and to move downwards with respect to the housing 302. The needle 334 thus extends through the aperture 356 in the carriage piece 335 and through the slot 336 in the lower housing part 306 to project from the contact face 312 and pierce the injection site.

Downward movement of the trigger button 450 also causes the legs 451 of the trigger button 450 (see FIG. 25, not visible in FIG. 30) to cooperate with the locking collar 389 to move the locking collar 389 into a recess 391 disposed at the rearward end of the slot 336 in the lower housing body 306. Thus the locking collar 389 no longer blocks relative movement between the hub 166 and the coupling element 22 of the cartridge 50.

Thus, once the locking collar 389 has moved into the recess 391 and the needle holder 332 has disengaged from the control piece 344, the control piece 344 can move rearwardly with respect to the housing 302, under the influence of the control spring 384. Rearward movement of the control piece 344 causes rearward movement of the hub 166 to move the hub 166 into a second attachment position with respect to the cartridge 50, as shown in FIG. 30(*b*), to switch the connection arrangement 399 to a connected configuration.

Thus, referring additionally to FIG. 31, when the hub 166 moves to the second attachment position, the piercing member 176 pierces the septum 16 of the cartridge 50 to open the outlet 15 to create a fluid flow path between the first chamber 14 of the cartridge 50 and the injection needle 334, as described above with reference to the first embodiment of the invention.

Upon continued movement of the trigger button 450 in the downward direction, from the intermediate position to a second position, the release pins 452 of the trigger button 450 engage with the arms 432 of the latching cap 414 of the delivery drive element 410. This causes the arms 432 to bend towards one another, releasing the clips 434 from the steps in the housing 302. As shown in FIG. 32, the delivery drive element 410 can now move forwardly along the drive axis A in a delivery stroke, under the bias of the delivery spring 420, to deliver the mixed substances from the first chamber 124 through the injection needle 334.

Once the delivery stroke is complete, the device 300 can be removed from the injection site and disposed of.

In summary, in an operating sequence of the device of the second embodiment of the invention, the shield 390 is first removed by the user. Removal of the shield exposes the needle 334 and causes mixing of the first and second substances within the device. The device can then be positioned against the injection site, and the trigger button 450 can be pressed by the user. Movement of the trigger button 450 first causes insertion of the needle 334 and switching of the connection arrangement 399 to the connected state, as the trigger button 450 moves through the intermediate position. When the trigger button 450 reaches the second position, the drive mechanism 400 is activated for delivery of the medicament. Thus, as in the first embodiment of the invention, only two user operations are required to initiate all of the steps in the operating sequence.

It will be appreciated that various features of the second embodiment could be applied in the first embodiment of the invention, and vice versa. For example, the linear-type drive mechanism and/or the button-type trigger assembly of the second embodiment could be adapted for use in the first embodiment. Similarly, the rotary-type drive mechanism and/or the slider-type trigger assembly of the first embodiment could be adapted for use in the second embodiment. Alternative drive mechanisms and trigger assemblies suitable for use in devices of the invention will also be known to those of skill in the art.

With suitable modification, the device of the second embodiment could be adapted for use with a single-container medicament cartridge, such as that used in the first embodiment of the invention. Similarly, the device of the first embodiment could be adapted for use with a two-container medicament cartridge of the type used in the second embodiment of the invention, with a suitable mechanism for performing a mixing stroke before delivery of the medicament.

The devices described above are intended to be disposed of after a single use. However, it is conceivable that the devices could be re-usable, with suitable features to allow re-setting of the drive elements and replacement of the medicament containers.

Devices according to the invention may include additional features as are generally known in the field. For example, to prevent contact with the needle after removal of the device from the injection site, a device according to the invention may include a deployable shroud arrangement that is disposed around the needle and that extends downwards to conceal the needle upon removal of the device. Alternatively, a mechanism for retracting the needle from the injection site automatically to shroud the needle in the housing after delivery of the medicament may be provided.

It is also conceivable that various features included in the above-described examples could be omitted. For example, for some applications, the connection arrangement may be omitted, in which case a fluid connection between the outlet of the cartridge and the needle may be established during assembly of the device.

In place of a hypodermic needle, devices according to the invention may comprise an alternative cannula, such as a flexible cannula, or may be adapted for use with such a cannula, an infusion set, or other suitable delivery means. In such cases, the above-described mechanisms for inserting the needle into the injection site may be modified (for example to facilitate automatic fluid connection to a cannula) or omitted.

Devices according to the invention may be used with cartridges that differ from the example described above, and the hub may cooperate with the cartridge to open the outlet and establish fluid communication in any suitable way. For example, in place of a pierceable septum, alternative means for sealing the outlet of the chamber may be provided, such as a releasable valve. The hub may therefore include a sealing element release member for cooperation with the sealing element to open the outlet. When the cartridge includes two containers, any suitable means for separating the substances in the initial state of the cartridge may be provided. For example, in place of a slit valve, an alternative closure for separating the first and second chambers may be provided. For instance, the first and second chambers could be separated by a membrane that can be split, detached or ruptured upon commencement of the mixing stroke.

It will be appreciated that the operational sequence of the devices could differ from the specific examples described above. For example, movement of the hub from the first attachment position to the second attachment position to establish fluid communication between the container and the injection needle (i.e. switching of the connection arrangement to the connected state) could occur before or after insertion of the injection needle to the injection site.

Switching of the connection arrangement to the connected state can be triggered by operation of any suitable operating member. The operating member may be operated manually by a user (as in the illustrated examples, in which switching of the connection arrangement is triggered by removal of a shield or by operation of a trigger arrangement). Alternatively, the operating member may be automatically operated. For example, the operating member may comprise a skin sensor that is operated by placement of the device against an injection site.

Any suitable means could be provided for driving relative movement of the cartridge and the hub to switch the connection arrangement to the connected state. Thus, in the illustrated examples, relative movement between the cartridge and the hub is driven by the control spring or by the container spring, but it is also conceivable that relative movement between the cartridge and the hub could be driven by the drive spring, or by a further spring that acts between the housing and the hub or between the housing and the cartridge. When a spring is used to drive relative movement between the hub and the housing, the spring may be a compression spring (as in the illustrated embodiments), or any other suitable type of spring, such as a tension spring, power spring or leaf spring. It is also conceivable that relative movement between the hub and the cartridge could be driven by means other than a spring, such as by cam or ramp arrangements.

In the illustrated examples, relative movement between the cartridge and the hub takes place along a connection axis that is parallel to the drive axis and perpendicular to the insertion direction of the needle. However, other arrangements are possible. For example, the insertion direction may be inclined with respect to the drive axis and/or the connection axis. It is also conceivable that the insertion direction could be parallel to or coaxial with the drive axis and/or the connection axis, to form a linear-type device.

It will also be appreciated from the above-described examples that the relative movement between the hub and the cartridge that takes place during switching of the connection arrangement to the connected state may involve movement of the hub with respect to the housing, movement of the cartridge with respect to the housing, or movement of both the hub and the cartridge with respect to the housing.

Thus, in some arrangements, the hub may be in a fixed position with respect to the housing at least during switching of the connection arrangement, and in other cases, the cartridge may be in a fixed position with respect to the housing at least during switching of the connection arrangement.

In embodiments in which two substances are mixed before injection, the mixing stroke may occur before or after insertion of the needle, and any suitable mechanism for triggering the mixing stroke may be provided. For example, in the second embodiment of the invention, the mixing stroke of the device is triggered by removal of the shield. However, in other embodiments, the mixing stroke could be triggered by another user-removable component, such as a pull tab or a packaging part. The mixing stroke could instead be triggered by operation of a trigger component such as a slider or button. For example, the mixing stroke could be triggered by operation of the same button as is provided for switching the connection arrangement, inserting the needle and activating the drive mechanism. The mixing element could comprise any suitable mixing means for causing relative movement of the first and second containers to perform the mixing stroke. For example, the mixing element could itself comprise a spring for driving relative movement of the containers.

Although some embodiments of the present invention are particularly useful for the reconstitution and delivery of a reconstitutable medicament, these embodiments can be equally useful in other applications in which two or more starting substances are to be mixed. It will be understood that, in the context of this specification, the term "mixture" is used to refer to any chemical or physical combination of two or more starting substances, and references to "mixing", "mixed" and related terms should be construed accordingly. Thus "mixing" should be taken to include the formation of a solution, suspension, emulsion, colloid, gel, sol, foam, and so on. The term "mixing" also includes the bringing together of two or more reactants that react together upon mixing to form a new chemical compound.

Further modifications and variations of the above-described examples are also possible without departing from the scope of the present invention as defined by the appended claims.

The invention claimed is:

1. A medicament delivery device for delivery of medicament from a cartridge into an injection site through a cannula, the cartridge comprising a first chamber having an outlet, and a sealing element for closing the outlet, the device comprising: a housing for receiving the cartridge; a drive mechanism comprising a drive element that is moveable with respect to the housing in a forward direction along a drive axis to expel the medicament from the device upon activation of the drive mechanism; and a connection arrangement comprising a hub and a spring for driving relative movement between the hub and the cartridge upon operation of an operating member of the device so as to switch the connection arrangement from an unconnected configuration in which the outlet is closed to a connected configuration in which the hub cooperates with the cartridge to open the outlet, thereby to establish a connection for fluid flow between the first chamber and the cannula, wherein the operating member comprises a shield for shielding the cannula, wherein the shield is moveable to expose the cannula, and wherein movement of the shield to expose the cannula releases the hub to move axially along a longitudinal axis of the medicament delivery device into the connected configuration.

2. The delivery device according to claim 1, further comprising a contact face for contact with the injection site for delivery of the medicament, wherein the drive axis is substantially parallel to the contact face.

3. The delivery device according to claim 1, wherein the spring comprises a compression spring.

4. The delivery device according to claim 1, further comprising a control mechanism for holding the connection arrangement in the unconnected configuration and for allowing relative movement between the cartridge and the hub upon operation of the operating member to switch the connection arrangement to the connected configuration.

5. The delivery device according to claim 1, wherein the shield is removable from the housing to expose the cannula.

6. The delivery device according to claim 1, the cannula comprising a hypodermic needle.

7. The delivery device according to claim 1, the device further comprising the cartridge.

8. A medicament disposed in the delivery device according to claim 1.

9. The delivery device according to claim 1, wherein the cartridge is moveable with respect to the housing to switch the connection arrangement from the unconnected configuration to the connected configuration.

10. The delivery device according to claim 9, wherein the spring biases the cartridge in the forward direction along the drive axis.

11. The delivery device according to claim 1, wherein the drive element is biased for movement in the forward direction.

12. The delivery device according to claim 11, further comprising a drive spring for biasing the drive element in the forward direction.

13. The delivery device according to claim 1, wherein the hub is moveable with respect to the housing.

14. The delivery device according to claim 13, wherein the hub is moveable with respect to the housing to switch the connection arrangement from the unconnected configuration to the connected configuration.

15. The delivery device according to claim 13, wherein the spring biases the hub in a rearward direction along the drive axis.

16. The delivery device according to claim 1, wherein the drive mechanism comprises a drive member that is rotatable with respect to the housing and a driver for driving rotation of the drive member.

17. The delivery device according to claim 16, wherein the driver comprises a power spring.

18. The delivery device according to claim 16, further comprising a transmission member for transferring force from the drive member to the drive element.

19. The delivery device according to claim 18, wherein the transmission member comprises a flexible chain.

20. The delivery device according to claim 1, further comprising a control piece for controlling relative movement between the hub and the housing.

21. The delivery device according to claim 20, wherein the control piece is coupled to the hub for joint movement with respect to the housing.

22. The delivery device according to claim 20, wherein the control piece is releasable for movement with respect to the housing upon operation of the operating member.

23. The delivery device according to claim 22, wherein the spring acts to bias the control piece for movement with respect to the housing.

24. The delivery device according to claim 20, further comprising a blocking formation for preventing movement of the control piece with respect to the housing, and wherein operation of the operating member causes disengagement of the blocking formation from the control piece to allow movement of the control piece with respect to the housing.

25. The delivery device according to claim 24, wherein the blocking formation is associated with the operating member.

26. The delivery device according to claim 24, further comprising:
a cannula holder that is moveable in an insertion direction with respect to the housing for extending the cannula into the injection site;
wherein the blocking formation is associated with the cannula holder; and
wherein movement of the cannula holder in the insertion direction causes disengagement of the blocking formation from the control piece.

27. The delivery device according to claim 1, wherein the hub is arranged for engagement with a coupling element disposed at an outlet end of the cartridge.

28. The delivery device according to claim 27, wherein the hub is engageable with the coupling element in a first attachment position in the unconnected configuration of the connection arrangement and in a second attachment position in the connected configuration of the connection arrangement.

29. The delivery device according to claim 27, wherein the hub comprises at least one clip for engagement with one or more respective engagement formations of the coupling element.

30. The delivery device according to claim 27, wherein the hub comprises a sealing element release member for cooperation with the sealing element of the cartridge to open the outlet when the connection arrangement is switched to the connected configuration.

31. The delivery device according to claim 30, wherein the sealing element release member comprises a piercing member for piercing the sealing element.

32. The delivery device according to claim 30, comprising a seal arrangement for forming a seal with the coupling element to enclose a tip of the sealing element release member in an enclosed chamber when the connection arrangement is in the unconnected configuration.

33. The delivery device according to claim 32, wherein the enclosed chamber is disposed on a forward side of the sealing element.

34. The delivery device according to claim 1, further comprising a trigger component that is moveable with respect to the housing to activate the drive mechanism.

35. The delivery device according to claim 34, wherein the trigger component comprises the operating member.

36. The delivery device according to claim 34, wherein the trigger component is moveable from a first position to a second position to activate the drive mechanism.

37. The delivery device according to claim 36, further comprising a trigger element for blocking operation of the drive mechanism, wherein movement of the trigger component to the second position causes movement of the trigger element to release the drive mechanism.

38. The delivery device according to claim 37, further comprising a lock member associated with the trigger component for holding the trigger element in engagement with a drive member of the drive mechanism, wherein movement of the trigger component to the second position causes disengagement of the trigger element from the drive member.

39. The delivery device according to claim 37, wherein the trigger element is biased to disengage from the drive mechanism.

40. The delivery device according to claim 37, further comprising a latch arrangement for latching the drive element in an initial position with respect to the housing, and wherein movement of the trigger component to the second position causes release of the latch arrangement to activate the drive mechanism.

41. The delivery device according to claim 40, further comprising a latch release formation associated with the trigger component and arranged for cooperation with a latch member of the drive element to release the latch arrangement upon movement of the trigger component to the second position.

42. The delivery device according to claim 36, further comprising a cannula holder, wherein the trigger component is moveable from the first position to an intermediate position to cause movement of the cannula holder in an insertion direction to insert the cannula and from the intermediate position to the second position to activate the drive mechanism.

43. The delivery device according to claim 42, further comprising a cartridge spring for biasing the cartridge in the forward direction with respect to the housing, and a latch arrangement for holding the cartridge in an initial position when the trigger component is in the first position and for releasing the cartridge for movement in the forward direction to cause insertion of the cannula upon movement of the trigger component to the intermediate position.

44. The delivery device according to claim 43, further comprising a carrier for receiving the cartridge, wherein the cartridge spring acts upon the carrier to bias the carrier and the cartridge in the forward direction.

45. The delivery device according to claim 43, wherein the spring comprises the cartridge spring.

46. The delivery device according to claim 1, further comprising a cannula holder that is moveable in an insertion direction with respect to the housing for extending the cannula into the injection site.

47. The delivery device according to claim 46, further comprising a flexible tube for providing a fluid connection between the hub and the cannula holder.

48. The delivery device according to claim 46, further comprising an insertion spring for driving movement of the cannula holder in the insertion direction.

49. The delivery device according to claim 46, wherein the insertion direction is non-parallel to the drive axis.

50. The delivery device according to claim 49, wherein the insertion direction is perpendicular to the drive axis.

51. The delivery device according to claim 46, further comprising a guide for guiding movement of the cannula holder in the insertion direction.

52. The delivery device according to claim 51, wherein the guide comprises a guide formation having a fixed position with respect to the housing.

53. The delivery device according to claim 51, wherein the guide comprises a guide formation that is moveable in the forward direction with respect to the housing.

54. The delivery device according to claim 53, further comprising a catch arrangement for latching the guide formation in a forward position with respect to the housing to prevent subsequent movement of the cannula holder along the drive axis.

55. The delivery device according to claim 46, further comprising a latch mechanism for latching the cannula holder in a retracted position and for releasing the cannula holder from the retracted position for movement of the cannula holder in the insertion direction.

56. The delivery device according to claim 55, wherein the latch mechanism comprises a latch release member associated with the operating member for releasing the cannula holder upon movement of the operating member relative to the housing.

57. The delivery device according to claim 55, further comprising a control piece for controlling relative movement between the hub and the housing, wherein the cannula holder is latched to the control piece when in the retracted position.

58. The delivery device according to claim 57, wherein the cannula holder comprises a latch member that is engageable with the control piece.

59. The delivery device according to claim 57, wherein the cannula holder is coupled to the control piece for movement with respect to the housing along the drive axis.

60. The delivery device according to claim 57, wherein the latch mechanism is arranged to release the cannula holder upon forward movement of the control piece with respect to the cannula holder.

61. The delivery device according to claim 60, wherein the control piece comprises a slot, and wherein the slot is shaped to release the latch member from the slot upon forward movement of the control piece.

62. The delivery device according to claim 1, wherein the cartridge further comprises a first container having the first chamber for a first substance, a second container telescopically received in the first container and having a second chamber for a second substance, a valve for closing a forward end of the second chamber and a rearward end of the first chamber, and a stopper for closing a rearward end of the second chamber; and
wherein the device further comprises a mixing element for causing displacement of the second substance into the first container through the valve in a mixing stroke of the device.

63. The delivery device according to claim 62, arranged such that the mixing stroke of the device is performed before switching of the connection arrangement to the connected configuration.

64. The delivery device according to claim 62, wherein the mixing element comprises a plunger that is moveable in the forward direction during the mixing stroke for cooperation with the stopper.

65. The delivery device according to claim 62, further comprising a mixing spring for biasing the mixing element in the forward direction.

66. The delivery device according to claim 62, wherein the drive element is arranged to move to the second container of the cartridge in the forward direction upon operation of the drive mechanism to expel the mixed first and second substances from the first chamber.

67. The delivery device according to claim 62, further comprising a clamp arrangement for securing the drive element to the second container.

68. The delivery device according to claim 62, wherein the drive element is arranged to hold the second container in an initial position with respect to the housing during the mixing stroke, such that the first container moves in the forward direction during the mixing stroke.

69. The delivery device according to claim 68, further comprising a cannula holder, wherein forward movement of the first container during the mixing stroke causes movement of the cannula holder along the drive axis to a forward position.

70. The delivery device according to claim 62, further comprising a latch mechanism for holding the mixing element in an initial position and for releasing the mixing element for movement upon release of the latch mechanism to start the mixing stroke of the device.

71. The delivery device according to claim 70, wherein the latch mechanism is releasable upon removal of a user-removable component.

72. The delivery device according to claim 71, wherein the user-removable component comprises a shield for shielding the cannula.

73. The delivery device according to claim 62, further comprising a locking arrangement for preventing switching of the connection arrangement to the connected configuration during the mixing stroke.

74. The delivery device according to claim 73, wherein the locking arrangement comprises a locking element and a recess for receiving the locking element at the end of the mixing stroke.

75. The delivery device according to claim 73, wherein the locking arrangement is arranged to couple the hub and the first container for joint movement with respect to the housing during the mixing stroke.

76. The delivery device according to claim 75, wherein the locking arrangement is releasable to allow relative movement of the hub and the first container at the end of the mixing stroke.

77. A method of treating a patient having a condition susceptible to treatment with the medicament, the method comprising:
dispensing an effective amount of the medicament to the patient utilizing the delivery device according to claim 1;
wherein the medicament is disposed in the cartridge and is dispensed into an injection site on the patient through the cannula.

* * * * *